US010806855B2

(12) United States Patent
Destefano et al.

(10) Patent No.: US 10,806,855 B2
(45) Date of Patent: Oct. 20, 2020

(54) RIGID NEEDLE INSERTION MECHANISM FOR A DRUG DELIVERY PUMP

(71) Applicant: UNL Holdings LLC, New York, NY (US)

(72) Inventors: Mark Destefano, Collegeville, PA (US); Ian Hanson, Wayne, PA (US); Paul Bente, Wayne, PA (US); Lawton Laurence, Phoenixville, PA (US)

(73) Assignee: UNL HOLDINGS LLC, New York, NY (US)

( * ) Notice: Subject to any disclaimer, the term of this patent is extended or adjusted under 35 U.S.C. 154(b) by 788 days.

(21) Appl. No.: 15/514,951

(22) PCT Filed: Sep. 29, 2015

(86) PCT No.: PCT/US2015/052815
§ 371 (c)(1),
(2) Date: Mar. 28, 2017

(87) PCT Pub. No.: WO2016/053954
PCT Pub. Date: Apr. 7, 2016

(65) Prior Publication Data
US 2017/0224915 A1    Aug. 10, 2017

Related U.S. Application Data

(60) Provisional application No. 62/056,890, filed on Sep. 29, 2014, provisional application No. 62/133,715, filed on Mar. 16, 2015.

(51) Int. Cl.
*A61M 5/158*      (2006.01)
*A61M 5/142*      (2006.01)

(52) U.S. Cl.
CPC ............ *A61M 5/158* (2013.01); *A61M 5/142* (2013.01); *A61M 5/14248* (2013.01);
(Continued)

(58) Field of Classification Search
CPC .. A61M 5/142; A61M 5/14248; A61M 5/158; A61M 5/321; A61M 5/322;
(Continued)

(56) References Cited

U.S. PATENT DOCUMENTS

| 3,336,924 A | 8/1967 | Sarnoff et al. |
| 3,401,692 A | 9/1968 | Harris, Jr. |

(Continued)

FOREIGN PATENT DOCUMENTS

| CN | 1245077 A | 2/2000 |
| CN | 101522235 A | 9/2009 |

(Continued)

OTHER PUBLICATIONS

European Patent Office, International Search Report in International Patent Application No. PCT/US2015/052815, dated Jan. 19, 2016, 6 pp.

(Continued)

*Primary Examiner* — Bhisma Mehta
*Assistant Examiner* — Larry R. Wilson
(74) *Attorney, Agent, or Firm* — Hamilton, Brook, Smith & Reynolds, P.C.

(57) ABSTRACT

An insertion mechanism and methods of assembly and operation of a drug pump may include an insertion mechanism housing; a housing cap; a manifold guide; an insertion biasing member initially held in an energized state; a retraction biasing member connected to a hub connected to a proximal end of a needle; and, optionally, a clip retainer. The retraction biasing member is held initially in an energized state between the hub and manifold guide. A manifold has a manifold body and one or more septa defining a manifold header. The retraction biasing member may be held initially energized between the hub and the clip retainer. The needle is advanced by the insertion biasing member(s) from the (Continued)

initial configuration to an administration configuration, opening a fluid pathway from the manifold header to the target. The pump may include an activation mechanism, a drive mechanism, a fluid pathway connection, and the insertion mechanism.

15 Claims, 17 Drawing Sheets

(52) U.S. Cl.
CPC .............. *A61M 2005/14252* (2013.01); *A61M 2005/14256* (2013.01); *A61M 2005/1585* (2013.01)

(58) Field of Classification Search
CPC .............. A61M 5/3232; A61M 5/3234; A61M 5/3276; A61M 2005/14252; A61M 2005/14256; A61M 2005/14284; A61M 2005/1581; A61M 2005/1585; A61M 2005/1857; A61M 2005/3208; A61M 2039/0291; A61M 5/14244
See application file for complete search history.

(56) References Cited

U.S. PATENT DOCUMENTS

| | | | |
|---|---|---|---|
| 3,413,974 A | 12/1968 | Cohen | |
| 3,778,971 A | 12/1973 | Granger et al. | |
| 3,940,003 A | 2/1976 | Larson | |
| 4,004,586 A | 1/1977 | Christensen et al. | |
| 4,048,997 A | 9/1977 | Raghavachari et al. | |
| 4,565,543 A | 1/1986 | Bekkering et al. | |
| 4,673,400 A | 6/1987 | Martin | |
| 4,685,903 A | 8/1987 | Cable et al. | |
| 4,755,173 A * | 7/1988 | Konopka .......... A61M 25/0606 128/DIG. 26 | |
| 4,840,620 A | 6/1989 | Kobayashi et al. | |
| 5,147,311 A | 9/1992 | Pickhard | |
| 5,167,816 A | 12/1992 | Kruger et al. | |
| 5,795,339 A | 8/1998 | Erskine | |
| 5,851,197 A | 12/1998 | Marano | |
| 5,858,001 A | 1/1999 | Tsals et al. | |
| 6,248,093 B1 | 6/2001 | Moberg | |
| 6,368,314 B1 | 4/2002 | Kipfer et al. | |
| 6,699,218 B2 | 3/2004 | Flaherty | |
| 7,063,684 B2 | 6/2006 | Moberg | |
| 7,250,037 B2 | 7/2007 | Shermer et al. | |
| D564,087 S | 3/2008 | Yodfat et al. | |
| D585,543 S | 1/2009 | Yodfat et al. | |
| 7,479,135 B2 | 1/2009 | Richter et al. | |
| D586,463 S | 2/2009 | Evans et al. | |
| 7,611,503 B2 | 11/2009 | Spohn et al. | |
| 7,780,636 B2 | 8/2010 | Radmer et al. | |
| 7,803,134 B2 | 9/2010 | Sharifi et al. | |
| D629,503 S | 12/2010 | Caffey et al. | |
| 7,846,132 B2 | 12/2010 | Gravesen et al. | |
| 7,879,010 B2 | 2/2011 | Hunn et al. | |
| 7,905,859 B2 | 3/2011 | Bynum et al. | |
| 7,927,306 B2 | 4/2011 | Cross et al. | |
| 7,967,795 B1 | 6/2011 | Cabiri | |
| 8,029,472 B2 | 10/2011 | Leinsing et al. | |
| 8,048,031 B2 | 11/2011 | Shaw et al. | |
| 8,152,771 B2 | 4/2012 | Mogensen et al. | |
| 8,157,769 B2 | 4/2012 | Cabiri | |
| 8,162,892 B2 | 4/2012 | Mogensen et al. | |
| 8,167,844 B2 | 5/2012 | Dillard, III | |
| 8,187,232 B2 | 5/2012 | Chong et al. | |
| D669,165 S | 10/2012 | Estes et al. | |
| 8,409,145 B2 | 4/2013 | Raymond | |
| D684,685 S | 6/2013 | Schneider et al. | |
| D684,686 S | 6/2013 | Cronenberg | |
| D685,083 S | 6/2013 | Schneider et al. | |
| 8,591,465 B2 | 11/2013 | Hommann | |
| D709,183 S | 7/2014 | Kemlein | |
| 8,795,234 B2 | 8/2014 | Kadamus et al. | |
| D723,157 S | 2/2015 | Clemente et al. | |
| 9,005,169 B2 | 4/2015 | Gravesen et al. | |
| D745,142 S | 12/2015 | O'Connor et al. | |
| D752,442 S | 3/2016 | O'Donahue | |
| 9,463,280 B2 | 10/2016 | Cabiri | |
| 9,511,189 B2 | 12/2016 | O'Connor et al. | |
| 2003/0199816 A1 | 10/2003 | Ramming | |
| 2004/0069044 A1 | 4/2004 | Lavi et al. | |
| 2004/0092878 A1 | 5/2004 | Flaherty | |
| 2007/0010789 A1 | 1/2007 | Peter et al. | |
| 2007/0179444 A1 | 8/2007 | Causey et al. | |
| 2007/0282269 A1 | 12/2007 | Carter et al. | |
| 2008/0065029 A1 | 3/2008 | Racz | |
| 2008/0132842 A1 | 6/2008 | Flaherty | |
| 2008/0269683 A1 | 10/2008 | Bikovsky | |
| 2008/0269687 A1 | 10/2008 | Chong et al. | |
| 2009/0124979 A1 | 5/2009 | Raymond et al. | |
| 2009/0204077 A1 | 8/2009 | Hasted et al. | |
| 2009/0240240 A1 | 9/2009 | Hines et al. | |
| 2010/0049129 A1 | 2/2010 | Yokoi et al. | |
| 2010/0331824 A1 | 12/2010 | Moberg et al. | |
| 2011/0054390 A1 | 3/2011 | Searle et al. | |
| 2011/0270188 A1 | 3/2011 | Caffey et al. | |
| 2011/0098652 A1 | 4/2011 | Hasted et al. | |
| 2011/0160678 A1 | 6/2011 | Chong et al. | |
| 2011/0166509 A1 | 7/2011 | Gross et al. | |
| 2011/0306929 A1 | 12/2011 | Levesque et al. | |
| 2012/0035546 A1 | 2/2012 | Cabiri | |
| 2012/0096953 A1 | 4/2012 | Bente, IV et al. | |
| 2012/0123354 A1 | 5/2012 | Wochr | |
| 2012/0211946 A1 | 8/2012 | Halili et al. | |
| 2013/0060196 A1 | 3/2013 | O'Connor et al. | |
| 2013/0060233 A1* | 3/2013 | O'Connor .......... A61M 5/14248 604/506 |
| 2013/0066274 A1 | 3/2013 | O'Connor et al. | |
| 2013/0131595 A1 | 5/2013 | Ekman et al. | |
| 2017/0080149 A1 | 3/2017 | O'Connor et al. | |

FOREIGN PATENT DOCUMENTS

| | | |
|---|---|---|
| CN | 101557847 A | 10/2009 |
| CN | 101631585 A | 1/2010 |
| CN | 101947337 A | 1/2011 |
| EP | 0589328 | 3/1994 |
| EP | 1219283 A2 | 7/2002 |
| EP | 1702635 A2 | 9/2006 |
| EP | 1341569 B1 | 1/2007 |
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2269559 A2 | 1/2011 |
| EP | 2331190 B1 | 6/2011 |
| EP | 2379134 | 10/2011 |
| EP | 2429612 | 3/2012 |
| EP | 2433663 A1 | 3/2012 |
| EP | 2731642 A | 9/2018 |
| JP | S62-201159 A | 9/1987 |
| JP | 2002-524217 A | 8/2002 |
| JP | 2003-527159 A | 9/2003 |
| JP | 2004-195227 A | 7/2004 |
| JP | 2004-528939 A | 9/2004 |
| JP | 2010-501211 A | 1/2010 |
| JP | 2010-501281 A | 1/2010 |
| JP | 2010-528810 A | 8/2010 |
| JP | 2010526633 A | 8/2010 |
| JP | 2010-531196 A | 9/2010 |
| JP | 2010-538751 A | 12/2010 |
| JP | 2011-045537 A | 3/2011 |
| JP | 2011-511689 A | 4/2011 |
| WO | WO 1995/019194 A1 | 7/1995 |
| WO | WO 1999/048546 A1 | 9/1999 |
| WO | WO 2000/015292 A2 | 3/2000 |
| WO | WO 00/29049 A1 | 5/2000 |
| WO | WO 2001/030424 A1 | 5/2001 |
| WO | WO 2003/024504 A2 | 3/2003 |
| WO | WO 2003/103763 A1 | 12/2003 |

(56) References Cited

FOREIGN PATENT DOCUMENTS

| | | |
|---|---|---|
| WO | WO 2004/035116 A1 | 4/2004 |
| WO | WO 2004/062714 A1 | 7/2004 |
| WO | WO 2005/037350 A2 | 4/2005 |
| WO | WO 2005/044344 A1 | 5/2005 |
| WO | WO 2006/129196 A1 | 12/2006 |
| WO | WO 2008/024808 A2 | 2/2008 |
| WO | WO 2008/024810 A2 | 2/2008 |
| WO | WO 2008/105954 A2 | 9/2008 |
| WO | WO 2008/133702 A1 | 11/2008 |
| WO | WO 2008/153460 A1 | 12/2008 |
| WO | WO 2009/039013 A1 | 3/2009 |
| WO | WO 2009/101145 A1 | 8/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | WO 2010/112377 A1 | 10/2010 |
| WO | WO 2010/132196 A1 | 11/2010 |
| WO | WO 2010/139672 A1 | 12/2010 |
| WO | WO 2011/006652 A1 | 1/2011 |
| WO | WO 2011/046950 A1 | 4/2011 |
| WO | WO 2011/090956 A2 | 7/2011 |
| WO | WO 2011/121023 A1 | 10/2011 |
| WO | WO 2012/032411 A2 | 3/2012 |
| WO | WO 2012/131044 A1 | 10/2012 |
| WO | WO 2013/033421 A1 | 3/2013 |
| WO | WO 2013/033467 A2 | 3/2013 |
| WO | WO 2013/156224 A1 | 10/2013 |
| WO | WO 2014/011879 A2 | 1/2014 |
| WO | WO 2016/053954 A1 | 4/2016 |

OTHER PUBLICATIONS

European Patent Office, Written Opinion in International Patent Application No. PCT/US2015/052815, dated Jan. 19, 2016, 6 pp.

International Preliminary Report on Patentability for International Application No. PCT/US2015/052815, entitled, "Rigid Needle Insertion Mechanism for a Drug Delivery Pump," date of completion: Mar. 13, 2017.

U.S. Food and Drug Administration, "Infusion Pump Improvement Initiative," Apr. 2010, 6 pp.

Meng et al., "MEMS-enabled implantable drug infusion pumps for laboratory animal research, preclinical, and clinical applications," Adv. Drug. Deliv. Rev., 64(14), Nov. 2012, pp. 1628-1638.

\* cited by examiner

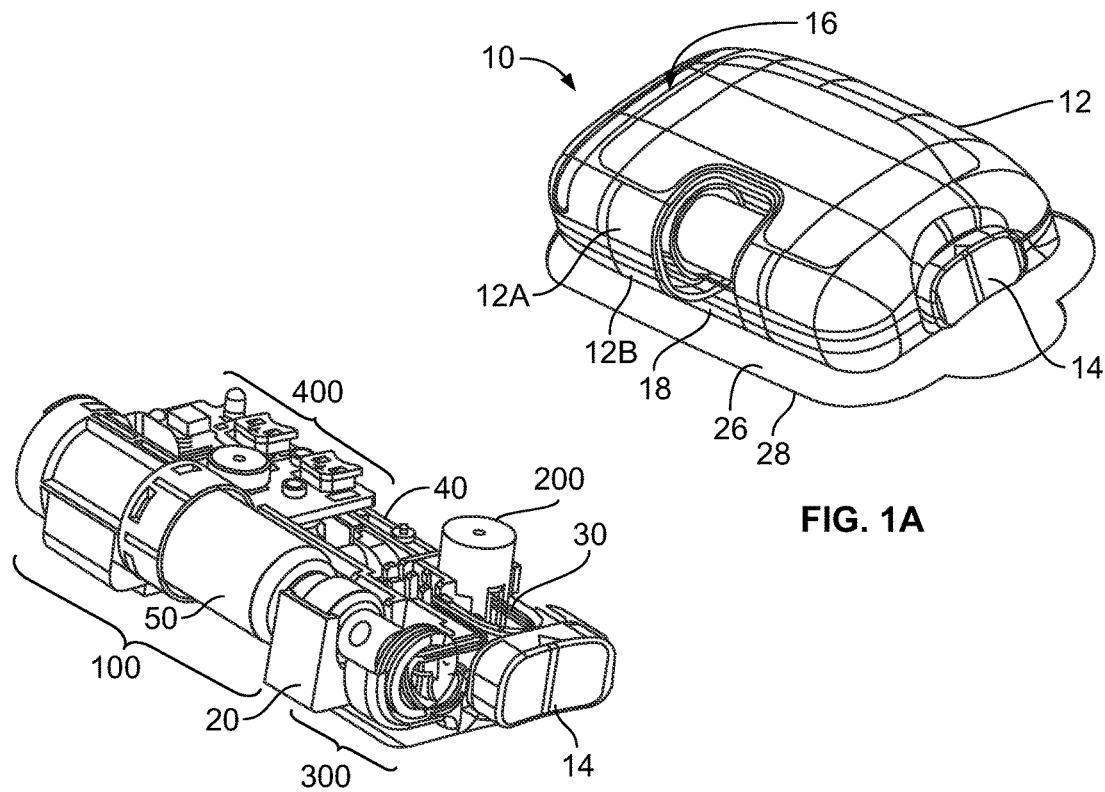
FIG. 1A
FIG. 1B
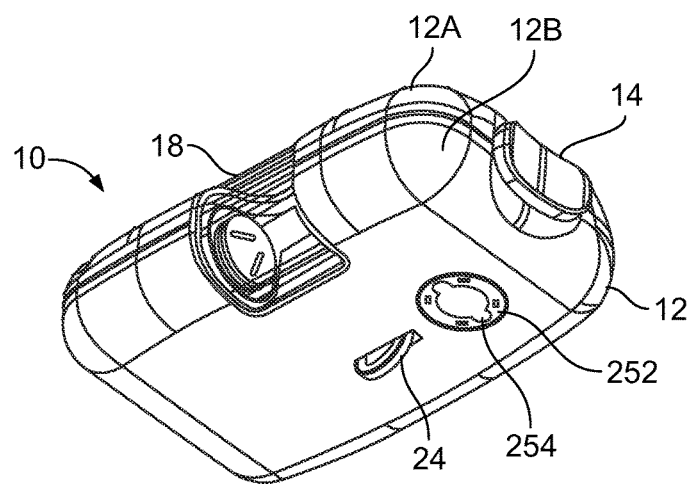
FIG. 1C

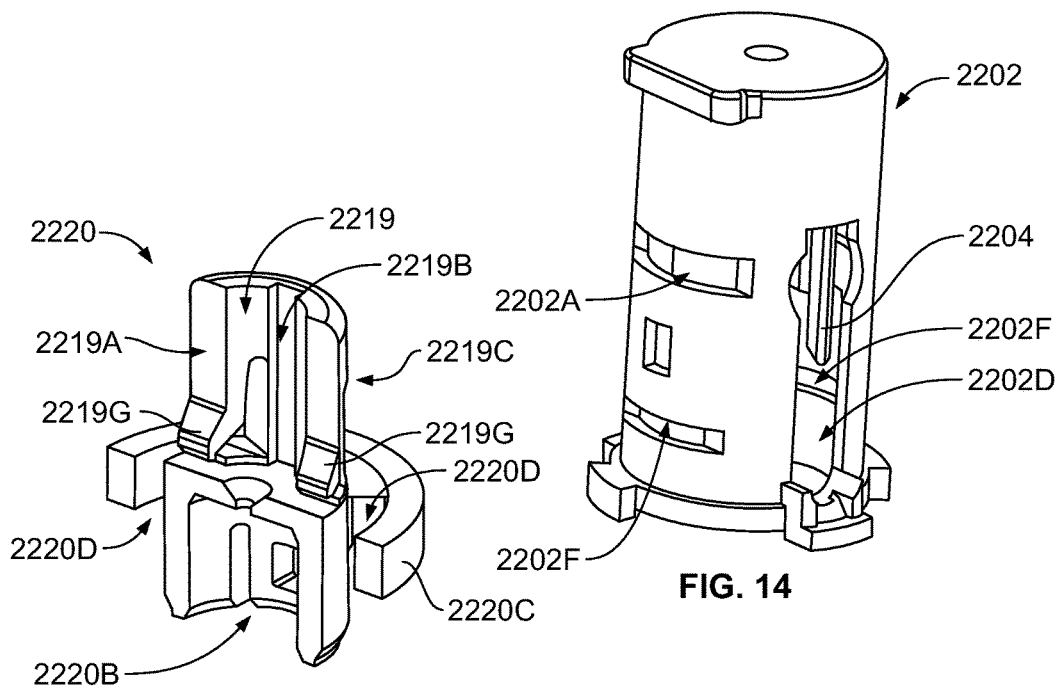
FIG. 15
FIG. 14
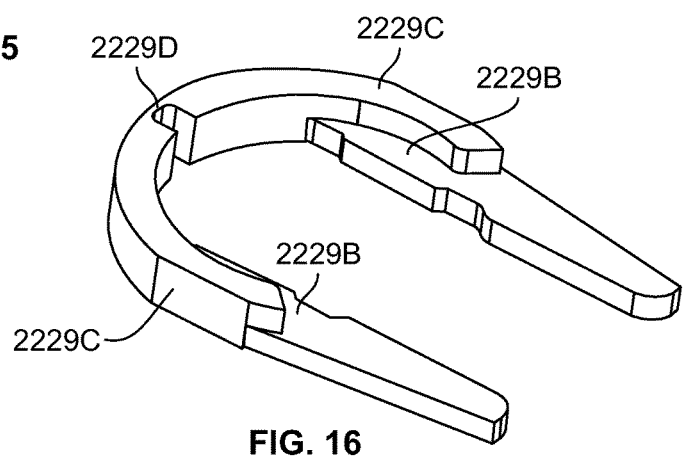
FIG. 16

RIGID NEEDLE INSERTION MECHANISM FOR A DRUG DELIVERY PUMP

CROSS-REFERENCE TO RELATED APPLICATIONS

This application is a national phase application of International Patent Application No. PCT/US2015/052815, filed Sep. 29, 2015, which claims priority to U.S. Provisional Application No. 62/056,890 filed on Sep. 29, 2014, and U.S. Provisional Application No. 62/133,715, filed Mar. 16, 2015, each of which is incorporated by reference herein in its entirety for all purposes.

FIELD

This invention relates to drug delivery pumps. More particularly, this invention relates to insertion mechanisms for drug delivery pumps, drug delivery pumps with safety integrated insertion mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian target, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a target. More recently, parenteral delivery of liquid medicines into a target has been accomplished by administering bolus injections using a needle and reservoir, continuously by gravity driven dispensers, or via transdermal patch technologies. Bolus injections often imperfectly match the clinical needs of patients, and usually require larger individual doses than are desired at the specific time they are given. Continuous delivery of medicine through gravity-feed systems compromises mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a target. These infusion devices have the ability to offer sophisticated fluid delivery profiles accomplishing bolus requirements, continuous infusion and variable flow rate delivery. These infusion capabilities usually result in better efficacy of the drug and therapy and less toxicity to a patient's system, for example. Currently available ambulatory infusion devices are expensive, difficult to program and prepare for infusion, and tend to be bulky, heavy and very fragile. Filling these devices can be difficult and require the user to carry both the intended medication as well as filling accessories. The devices often require specialized care, maintenance, and cleaning to assure proper functionality and safety for their intended long-term use, and are not cost-effective for users or healthcare providers.

As compared to syringes and injection pens, pump type delivery devices can be significantly more convenient in that doses of the drug may be calculated and delivered automatically to a target at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of target needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and users a small, low cost, light weight, simple to use alternative for parenteral delivery of liquid medicines.

SUMMARY

The present invention provides insertion mechanisms for drug delivery pumps, drug delivery pumps with safety integrated insertion mechanisms, the methods of operating such devices, and the methods of assembling such devices. The insertion mechanisms of the present invention may provide integrated safety features which automatically retract the needle into the device upon removal of the device from the target. Additionally, the embodiments of the present invention provide sterile fluid pathways through the novel insertion mechanisms and drug pumps, which pathways are only engaged, connected, or opened upon proper activation by the user. Accordingly, the novel devices of the present invention alleviate one or more of the problems associated with prior art devices, such as those referred to above.

In a first embodiment, the present invention provides an insertion mechanism for a drug pump, said insertion mechanism including: an insertion mechanism housing having an internal chamber; a manifold guide having an upper chamber and a lower chamber separated by a manifold guide ring; one or more insertion biasing members initially held in an energized state within the internal chamber of insertion mechanism housing between the housing cap and the manifold guide ring; a clip flexibly engaged with the upper chamber of the manifold guide; a retraction biasing member and a hub connected to a proximal end of a needle, wherein the refraction biasing member is held initially in an energized state between the hub and the manifold guide; and a manifold having one or more septa, wherein the annular space between the septa defines a manifold header.

In an alternative embodiment, the insertion mechanism may include two or more insertion biasing members. The manifold has a manifold intake for connection to a fluid conduit. The insertion mechanism further includes a travel limiter, engaged with the housing, at least a portion of which is located within the housing internal chamber.

In another embodiment, the present invention provides an insertion mechanism for a drug pump, said insertion mechanism including: an insertion mechanism housing having an internal chamber; a housing cap engaged with the housing; a clip retainer including an internal chamber and a flange; a manifold guide having an internal chamber and a manifold guide ring; one or more insertion biasing members initially held in an energized state within the internal chamber of the insertion mechanism housing between the housing cap and the clip retainer flange; a clip flexibly engaged with the internal chamber of the clip retainer; a retraction biasing member and a hub connected to a proximal end of a needle, wherein the refraction biasing member is held initially in an energized state between the hub and the clip retainer; and a manifold having one or more septa, wherein the annular space between the septa defines a manifold header. In an alternative embodiment, the insertion mechanism may include two or more insertion biasing members. The manifold has a manifold intake for connection to a fluid conduit. The insertion mechanism further includes a travel limiter, engaged with the housing, at least a portion of which is located within the housing internal chamber.

The insertion mechanism may further include a base connected to a distal end of the insertion mechanism housing. A sterile boot may be fixedly connected between the manifold and the base connected to a distal end of the insertion mechanism housing. The term "sterile boot" is used to describe a boot within which certain internal components may reside, at one or more stages of operation, in a sterile condition. The boot need not be sterile through the entire operation of the mechanism or pump and, in fact, may not be initially sterile until assembly and sterilization of certain components has occurred. Additionally, the term "boot" is not intended to mean any specific shape or configuration, but is instead utilized to describe a component that can provide an interior space within which other components may reside at one or more stages of operation.

One or more guide protrusions may extend from a proximal end of the insertion mechanism housing or housing cap into the internal chamber. Alternatively, the one or more guide protrusions may be a separate component that is fixed to the insertion mechanism housing. The manifold guide ring and/or clip retainer flange has one or more pass-throughs which correspond with the guide protrusions, wherein the manifold guide and/or the clip retainer is slidably engaged with the housing by interaction between the pass-throughs and the guide protrusions. The interaction between the pass-throughs and the guide protrusions may also function to maintain the rotational alignment of the manifold guide and/or to promote proper assembly of the components.

The clip may have one or more arms, with each arm having a release surface and a lockout surface. In an initial locked configuration the release surfaces engage the hub to maintain the retraction biasing member in an energized state; and, in a retracted configuration the release surfaces disengage the hub to permit de-energizing of the retraction biasing member, thereby retracting the hub and the needle. The manifold and manifold guide and clip retainer are maintained in their final positions and prevented from axial translation in the proximal direction by interaction between the lockout surfaces of the clips and the distal ends of the guide protrusions, effectively locking out further motion of these components. In some embodiments, the clip is caused or allowed to transform from the locked configuration to the retracted configuration by transformation of the travel limiter from a first configuration to a second configuration. In the first configuration, the travel limiter restricts distal movement of the manifold guide and prevents the release surfaces of the clip from disengaging from the hub. In the second configuration, the travel limiter allows some additional distal movement of the manifold guide which allows the release surfaces of the clip to disengage the hub. In other embodiments, the clip retainer is rotated from a first position to a second configuration; this rotation is transmitted to the clip. In the first configuration, the release surfaces of the clip are prevented from disengaging the hub. In the second configuration, the release surfaces of the clip are not prevented from disengaging the hub.

In another embodiment, the present invention provides a drug delivery pump with integrated safety features including a housing and an assembly platform, upon which an activation mechanism, a drive mechanism, a fluid pathway connection, a power control system, and an insertion mechanism for a drug pump may be mounted, said insertion mechanism including: an insertion mechanism housing having an internal chamber; a manifold guide having an upper chamber and a lower chamber separated by a manifold guide ring; one or more insertion biasing members initially held in an energized state within the internal chamber of insertion mechanism housing between the housing cap and the manifold guide ring; a clip flexibly engaged with the upper chamber of the manifold guide; a retraction biasing member and a hub connected to a proximal end of a needle, wherein the retraction biasing member is held initially in an energized state between the hub and the manifold guide; a manifold having one or more septa, wherein the annular space between the septa defines a manifold header; a travel limiter engaged with insertion mechanism housing and a base for connection of the insertion mechanism to the assembly platform.

In another embodiment, the present invention provides a drug delivery pump with integrated safety features including a housing and an assembly platform, upon which an activation mechanism, a drive mechanism, a fluid pathway connection, a power control system, and an insertion mechanism for a drug pump may be mounted, said insertion mechanism including: an insertion mechanism housing having an internal chamber; a housing cap attached to the housing; a clip retainer having an internal chamber and a flange; a manifold guide having an internal chamber and a manifold guide ring; one or more insertion biasing members initially held in an energized state within the internal chamber of the insertion mechanism housing between the housing cap and the manifold guide ring; a clip flexibly engaged with the internal chamber of the clip retainer; a retraction biasing member and a hub connected to a proximal end of a needle, wherein the retraction biasing member is held initially in an energized state between the hub and the clip retainer; a manifold having one or more septa, wherein the annular space between the septa defines a manifold header; a travel limiter engaged with the insertion mechanism housing; and a base for connection of the insertion mechanism to the assembly platform.

The insertion mechanism of the drug pump may further include a base connected to a distal end of the insertion mechanism housing. The manifold may have a manifold intake for connection to a fluid conduit, wherein the fluid conduit is employable for fluid transfer between the fluid pathway connection and the insertion mechanism. A sterile boot may be fixedly connected between the manifold and the base connected to a distal end of the insertion mechanism housing. These components function to maintain the sterility of the fluid pathway and the needle, prior to insertion into the target.

In a further embodiment, the present invention provides a method of assembling the insertion mechanism including the steps of: connecting a hub to a proximal end of a needle; inserting the hub and needle into an inner upper chamber of a manifold guide, wherein a retraction biasing member is maintained in an energized state between the manifold guide and the hub, and maintained in the energized state by a clip fixedly and flexibly connected to the manifold guide at a clip interface. The method further includes: inserting one or more septa into the manifold to create a manifold header there-between, and subsequently inserting the manifold and septa into a lower chamber of the manifold guide such that the needle pierces through at least one septum and resides initially at least partially within the manifold header. Furthermore, the method includes: inserting an insertion biasing member into an insertion mechanism housing between the housing and one or more guide protrusions extending into the interior of the housing from a proximal end or from a housing cap; inserting the manifold guide into the insertion mechanism housing such that the guide protrusions extend through corresponding pass-throughs on a manifold guide ring aspect of the manifold guide, wherein as the manifold guide is translated in the proximal direction, the insertion biasing member is caused to contact the manifold guide ring and become energized.

In an alternative embodiment, the present invention provides a method of assembling the insertion mechanism includes the steps of: connecting a hub to a proximal end of a needle; inserting the hub and needle into an internal chamber of a clip retainer, wherein a retraction biasing member is maintained in an energized state between the clip retainer and the hub, and maintained in the energized state by a clip fixedly and flexibly connected to the clip retainer at a clip interface. The method further includes: inserting one or more septa into the manifold to create a manifold header there-between, and subsequently inserting the manifold and septa into an internal chamber of a manifold guide such that the needle pierces through at least one septum and resides initially at least partially within the manifold header. Furthermore, the method includes: inserting an insertion biasing member into an insertion mechanism housing between the housing and one or more guide protrusions extending into the interior of the housing from a proximal end or from a housing cap; inserting the clip retainer and manifold guide into the insertion mechanism housing such that the guide protrusions extend through corresponding pass-throughs on a flange of the clip retainer and manifold guide ring aspect of a manifold guide, wherein as the clip retainer and manifold guide are translated in the proximal direction, the insertion biasing member is caused to contact the clip retainer flange and become energized.

Upon translation of the manifold guide and/or clip retainer and compression of the insertion biasing member to a point above one or more lockout windows of the insertion mechanism housing, the method includes the step of: placing one or more corresponding lockout pin(s) into the lockout windows and in removable engagement with the manifold guide to retain the manifold guide in this position and the insertion biasing member in the energized state. Finally, a base may be attached to the distal end of the insertion mechanism housing to maintain the components in position. The method of assembly may further include the step of: attaching a sterile boot in fixed engagement at a proximal end to the manifold and in a fixed engagement at a distal end to the base. Similarly, the method may include: attaching a fluid conduit to the manifold at a manifold intake. The method of assembly may further include the step of: attaching a travel limiter to the housing such that at least a portion of the travel limiter is located internal to the housing.

In yet another embodiment, the present invention provides a method of operating the drug delivery pump. The method of operation includes: displacing an activation mechanism to disengage one or more lockout pins from corresponding lockout windows of an insertion mechanism housing, wherein such disengagement permits an insertion biasing member to expand in a distal direction substantially along a longitudinal axis of the insertion mechanism housing from its initial energized state, wherein such expansion drives insertion of a needle into the target; connecting a fluid pathway connection having a piercing member to a drug container having a pierceable seal; and activating a drive mechanism to force a fluid through the fluid pathway connection, the needle, and into the target. The method further includes: disengaging one or more release surfaces of a clip from engagement with a hub retained within a manifold guide or clip retainer within the insertion mechanism housing, wherein such disengagement permits a retraction biasing member to expand in a proximal direction substantially along a longitudinal axis of the insertion mechanism housing from its initial energized state, wherein such expansion drives refraction of the needle. In a preferred embodiment, the method of operation may include: first displacing one or more sensors to permit displacement of the activation mechanism. The method may include one or more additional steps to activate the retraction of the needle. These steps may be performed by the user such as, for example, displacing a second activation member or may be automatically performed by the drug pump upon completion of dose delivery, failure or fault of the drive mechanism, or removal of the drug pump from the target.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 1A is an isometric view of a drug delivery pump having safety integrated insertion mechanisms, according to one embodiment of the present invention;

FIG. 1B is an isometric view of the interior components of the drug delivery pump shown in FIG. 1A;

FIG. 1C is an isometric view of the bottom of the drug delivery pump shown in FIG. 1A;

FIG. 14 is an isometric view of an insertion mechanism housing, according to at least one embodiment of the present invention;

FIG. 15 is an isometric view of a manifold guide according to at least one embodiment of the present invention;

FIG. 16 is an isometric view of a travel limiter of at least one embodiment of the present invention;

DETAILED DESCRIPTION

Figure 2A:
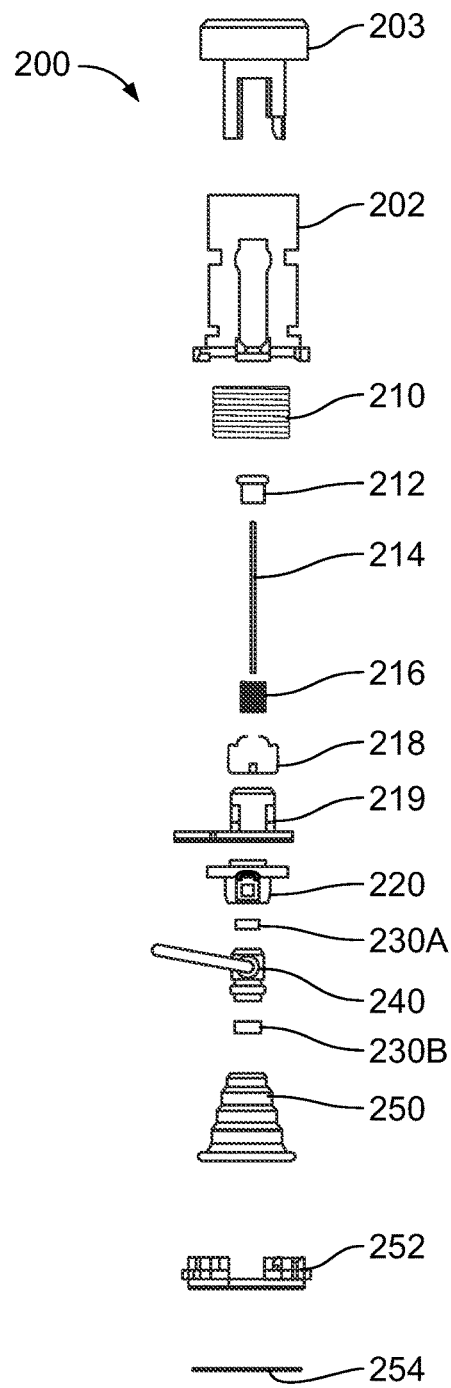
FIG. 2A is an exploded view of an insertion mechanism, according to a first embodiment of the invention.

As used herein to describe the insertion mechanisms, drug delivery pumps, or any of the relative positions of the components of the present invention, the terms "axial" or "axially" refer generally to a longitudinal axis "A" around which the insertion mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide insertion mechanisms with integrated safety features and drug delivery pumps which incorporate such insertion mechanisms. Such devices are safe and easy to use, and are aesthetically and ergonomically appealing for self-administering users. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pump, insertion mechanism, and their respective components are described further herein with reference to the accompanying figures.

Drug Delivery Pump:

As used herein, the term "pump" is intended to include any number of drug delivery systems which are capable of dispensing a fluid to a target upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a target. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump 10 further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the target. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the target. Housing 12 is described in further detail hereinafter with reference to other components and embodiments of the present invention.

Drug pump 10 is configured such that, upon activation by a user by depression of the activation mechanism, the drug pump is initiated to: insert a fluid pathway into a target; enable, connect, or open necessary connections between a drug container, a fluid pathway, and a sterile fluid conduit; and force drug fluid stored in the drug container through the fluid pathway and fluid conduit for delivery into a target. The target may be, for example an object such as a tissue.

One or more optional safety mechanisms may be utilized, for example, to prevent premature activation of the drug pump. For example, an optional sensor 24 (shown in FIG. 1C) may be provided in one embodiment as a safety feature to ensure that the power and control system 400, or the activation mechanism 14, cannot be engaged unless the drug pump 10 is in contact with the target. In one such embodiment, the sensor 24 is located on the bottom of lower housing 12B where it may come in contact with the target. Upon displacement of the sensor 24, depression of the activation mechanism is permitted. Accordingly, in at least one embodiment the sensor 24 is a mechanical safety mechanism, such as for example a mechanical lock out, that prevents triggering of the drug pump 10 by the activation mechanism 14. In another embodiment, the sensor may be an electro-mechanical sensor such as a mechanical lock out that sends a signal to the power and control system 400 to permit activation. In still other embodiments, the sensor can be electrically based such as, for example, a capacitive- or impedance-based sensor which must detect the presence of a target, such as a tissue, before permitting activation of the power and control system 400. These concepts are not mutually exclusive and one or more combinations may be utilized within the breadth of the present invention to prevent, for example, premature activation of the drug pump. Additionally, or alternatively, sensor 24, in combination with any of the above concepts may be used to retract the needle from the target if the sensor signals that drug pump 10 is no longer in contact with the target. This feature may reduce the risk of needle-stick injuries. In a preferred embodiment, the drug pump 10 utilizes one or more mechanical sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the sensor and/or trigger mechanism have been pressed, the power and control system 400 provides a ready-to-start status signal via the status indicator 16 if device start-up checks provide no errors. After providing the ready-to-start status signal and, in an embodiment with the optional sensor, if the sensor remains in contact with the target, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14.

During the drug delivery process, the power and control system 400 is configured to provide a dispensing status signal via the status indicator 16. After the drug has been administered into the target and after the end of any additional dwell time, to ensure that substantially the entire dose has been delivered to the target, the power and control system 400 may provide an okay-to-remove status signal via the status indicator 16. This may be independently verified by the user by viewing the drive mechanism and drug dose delivery through the window 18 of the pump housing 12.

Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation.

Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

The fluid pathway connection 300 includes a sterile fluid conduit 30, a piercing member, a connection hub, and a sterile sleeve. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the target.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In a preferred embodiment, this connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Drive Mechanism:

The drive mechanism 100 includes drug container 50 having a cap, a pierceable seal, and a plunger seal. The drug container may contain a drug fluid, within the container between the cap and the plunger seal, for delivery through the insertion mechanism and drug pump into the target. The drive mechanism may further include one or more drive biasing members, one or more release mechanisms, and one or more guides. The components of the drive mechanism function to force a fluid from the drug container out through the pierceable seal or, preferably, through the piercing member of the fluid pathway connection for delivery through the fluid pathway connection, sterile fluid conduit, and insertion mechanism into the target.

The drive mechanism may further include one or more electrical contacts located on corresponding components which, upon contact between electrical contacts, are capable of continuing an energy pathway or otherwise relay a signal to and/or from the power and control system 400. Such signals may be transferred across one or more interconnects. Such components may be utilized within the drive mechanism to measure and relay information related to the status of operation of the drive mechanism, which may be converted by the power and control system 400 into tactile, auditory, and/or visual feedback to the user.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The fluid pathway connection is connected through the pierceable seal prior to, concurrently with, or after activation of the drive mechanism to permit fluid flow from the drug container, through the fluid pathway connection, sterile fluid conduit, and insertion mechanism, and into the target for drug delivery. In at least one embodiment, the fluid flows through only a manifold and a needle of the insertion mechanism, thereby maintaining the sterility of the fluid pathway before and during drug delivery. Such components and their functions are described in further detail hereinafter.

Figure 2B:
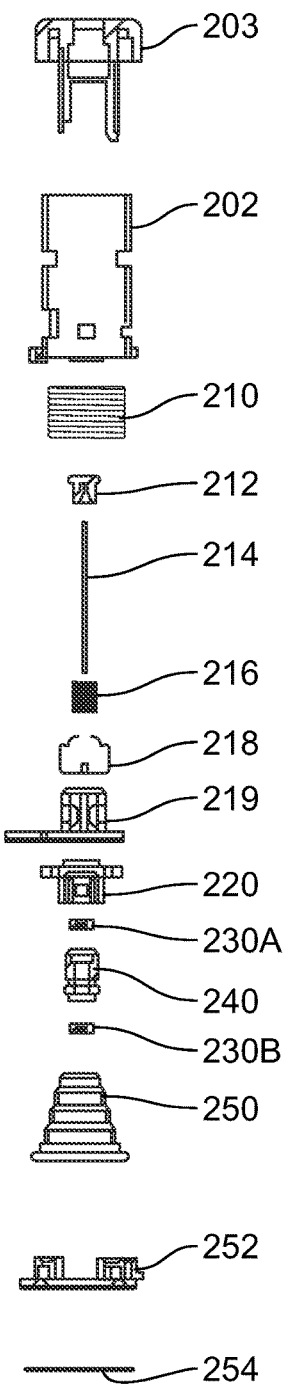
FIG. 2B is a cross-sectional exploded view of the insertion mechanism of FIG. 2A.

Insertion Mechanism:

In one embodiment, the insertion mechanism 200 includes an insertion mechanism housing 202, a housing cap 203, a base 252, and a sterile boot 250, as shown in FIG. 2A. Base 252 may be connected to assembly platform 20 to integrate the insertion mechanism into the drug pump 10 (as shown in FIG. 1B). The connection of the base 252 to the assembly platform 20 may be, for example, such that the bottom of the base is permitted to pass through a hole in the assembly platform to permit direct contact of the base to the target. In such configurations, the bottom of the base 252 may include a sealing membrane 254 that, at least in one embodiment, is removable prior to use of the drug pump 10. Alternatively, the sealing membrane 254 may remain attached to the bottom of the base 252 such that the hollow needle 214 pierces the sealing membrane 254 during operation of the drug pump 10. As shown in FIGS. 2A and 2B, the insertion mechanism 200 may further include an insertion biasing member 210, a hub 212, a needle 214, a retraction biasing member 216, a clip 218, a clip retainer 219, a manifold guide 220, septa 230A and 230B, and a manifold body 240. The manifold 240 may connect to sterile fluid conduit 30 to permit fluid flow through the manifold 240, into an interior of the hollow needle 214, and into the target during drug delivery, as will be described in further detail herein.

Figure 3:
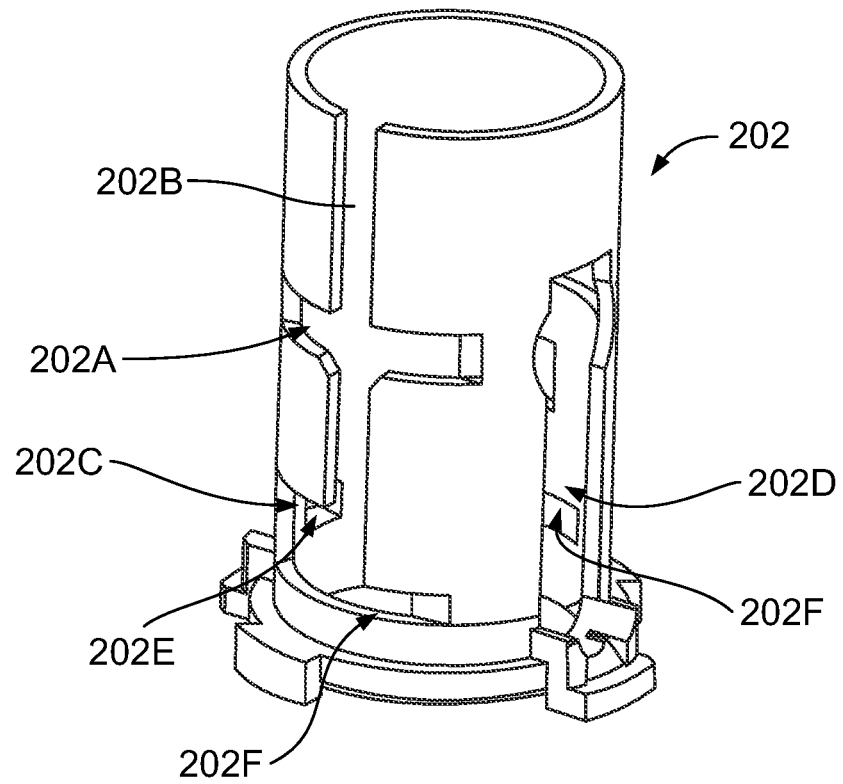
FIG. 3 is an isometric view of an insertion mechanism housing, according to at least one embodiment of the present invention.

FIGS. 3-9 show the components of the insertion mechanism, according to at least a first embodiment, in greater detail. As shown in FIG. 3, insertion mechanism housing 202 may be a substantially cylindrical component having an inner chamber within which the components of the insertion mechanism are substantially housed. Housing 202 further includes axial slot 202B within which protrusion 219H of clip retainer 219 slidably translates during insertion as will be described in greater detail hereinafter. Housing 202 may further include circumferential slot 202C which allows protrusion 219H to be rotated to allow retraction biasing member 216 to retract needle 214. Housing 202 may further include axial slot 202D within which sterile fluid conduit 30 may translate during needle insertion. Housing 202 further includes one or more lockout windows 202A which are configured to engage lockout pins 208 in an initial, locked configuration. Lockout pins 208 may pass through windows 202A to the interior of housing 202 such that manifold guide ring 220C may rest upon lockout pins 208 in an initial, locked configuration. Housing 202 may additionally include limiter slots 202F and aperture 202E which are configured to accept and engage travel limiter 229. Alternatively, the protrusion 219H may be replaced by a manual button or the like, or an automated or automatic mechanism that responds to a timer or other control system or method (not shown).

Figure 4:
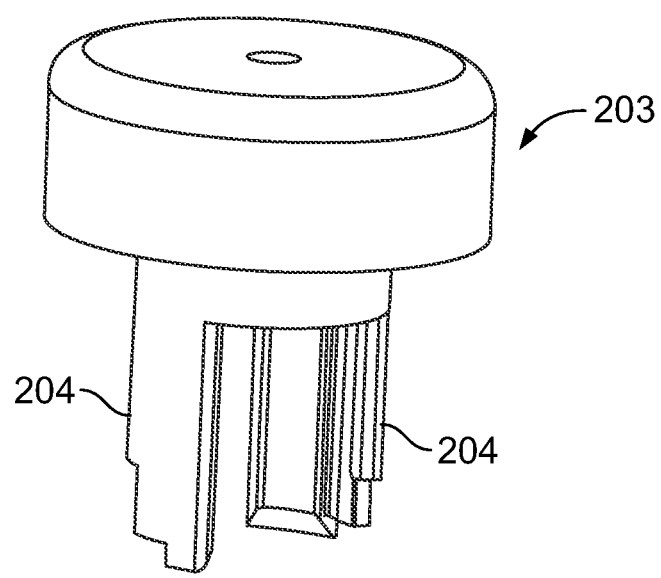
FIG. 4 is an isometric view of an insertion mechanism housing cap, according to at least one embodiment of the present invention.

Housing cap 203, shown in FIG. 4, contains guide protrusions 204. Guide protrusions 204 may, alternatively, be a pre-formed aspect on the interior of insertion mechanism housing 202. The guide protrusions 204 slidably engage clip retainer 219 at pass throughs 219D and may slidably engage manifold guide 220 at pass-throughs 220D on manifold guide ring 220C. The insertion biasing member 210 initially resides in an energized state between the guide protrusions 204 and inner surface of insertion mechanism housing 202 and between the interior proximal end of the insertion mechanism housing cap 203 and the flange 219E of clip retainer 219. Therefore upon activation by the user, as described further hereinafter, the insertion biasing member 210 is caused to bear against and exert force upon flange 219E of clip retainer 219 as the insertion biasing member 210 decompresses and/or de-energizes, causing axial translation in the distal direction of the clip retainer 219, clip 218, hub 212, retraction biasing member 216, manifold guide 220 and the components retained within manifold guide lower chamber 220E. Prior to activation, the insertion biasing member 210 is maintained substantially above locking windows 202A in a compressed, energized state. Housing cap 203 may be mounted to housing 202 by any means known to one skilled in the art such as threading, bonding, ultrasonic welding, press-fit, snap-fit, etc.

Figure 5:
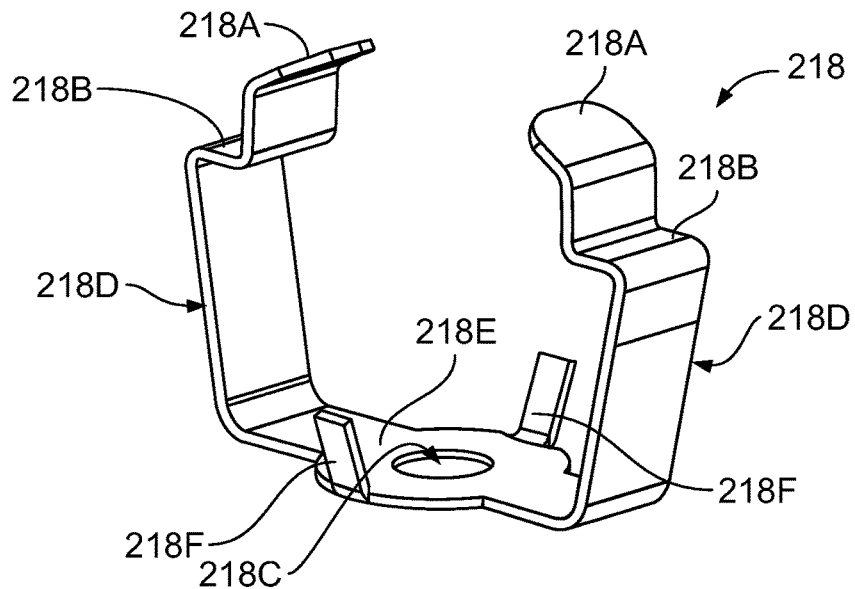
FIG. 5 is an isometric view of a clip, according to at least one embodiment of the present invention.
Figure 8:
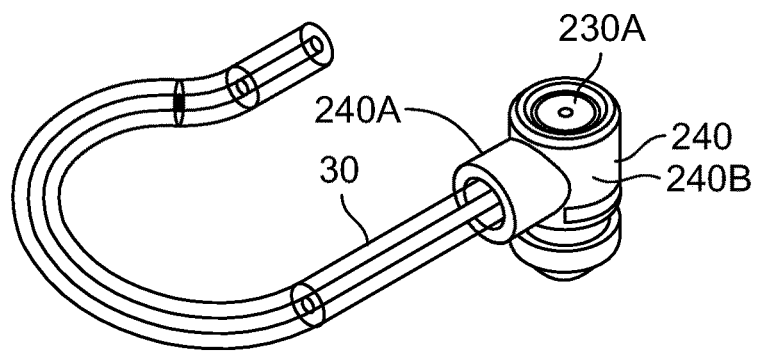
FIG. 8 is an isometric view of a manifold and fluid conduit according to at least one embodiment of the present invention.

FIG. 5 shows a clip 218, according to one embodiment of the present invention. Clip 218 includes aperture 218C through face 218E through which needle 214 may pass, and release surfaces 218A and lockout surfaces 218B of arms 218D. Clip 218 further includes prongs 218F. Clip 218 may be made of any number of resilient materials that are capable of flexing and returning to substantially their original form. In an original form, clip 218 may flex outwards such that arms 218D are not perpendicular with face 218E. Clip 218 resides within clip retainer 219 such that clip 218 is in fixed engagement with clip retainer 219 but arms 218D are permitted to flex within slots 219A. Prongs 218F are configured to engage slots 219F of clip retainer 219, thus coupling rotation of clip 218 and clip retainer 219. In an initial locked stage, retraction biasing member 216 and hub 212 (with connected needle 214) are retained between release surfaces 218A and face 218E of clip 218, and within inner chamber 219B of clip retainer 219. The needle may pass through aperture 218C of clip 218, through aperture 219G of clip retainer 219, and through manifold guide 220 into septa 230 and manifold 240. Septa 230 reside within manifold 240, as shown in FIG. 8. Manifold 240 further includes a manifold body 240B having a manifold intake 240A at which the sterile fluid conduit 30 may be connected. This connection is such that the sterility is maintained from the drug container 50 of the drive mechanism 100, through the fluid pathway connection 300 and the sterile fluid conduit 30, into sterile manifold header 242 of manifold 240 and sterile boot 250 to maintain the sterility of the needle 214, and the fluid pathway until insertion into the target for drug delivery.

Figure 6:
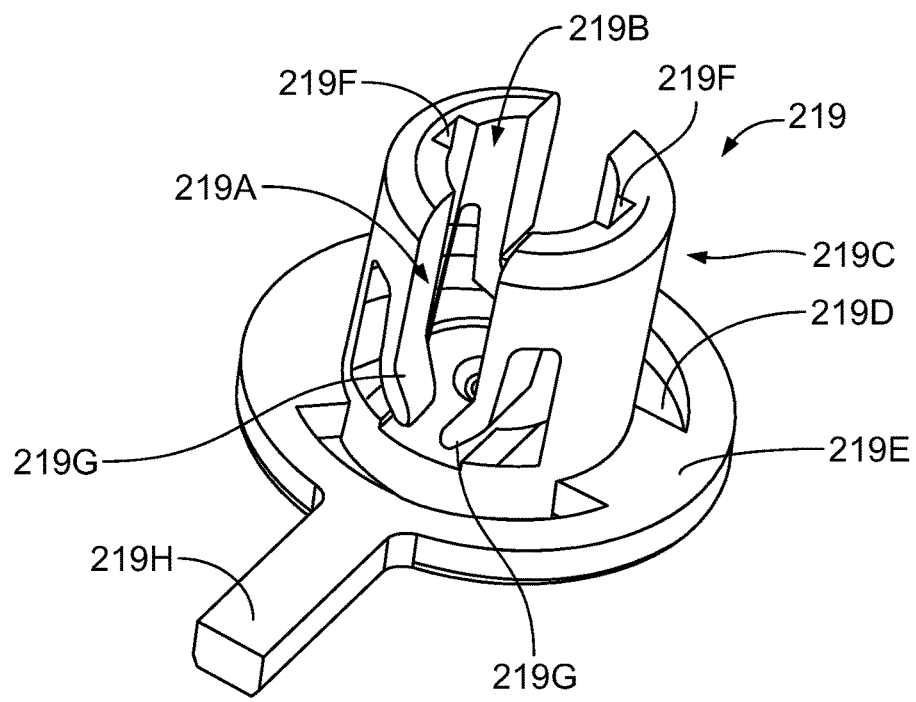
FIG. 6 is an isometric view of a clip retainer according to at least one embodiment of the present invention.

The clip retainer 219, shown in FIG. 6 may include a clip interface slot 219A for engageable retention of clip 218, shown in FIG. 5. Flexible extensions 219G may be configured to flex outward during installation of clip 218 into clip interface slot 219A and, upon clip insertion, return to their natural positions. Hence, the clip 218 is substantially retained in axial position with respect to clip retainer 219. The clip retainer 219 may have an inner chamber 219B, within which the retraction biasing member 216, the clip 218, and the hub 212 may reside during an initial locked stage of operation, and an outer upper chamber 219C, which interfaces with the insertion biasing member 210. In at least one embodiment, the insertion biasing member 210 and the retraction biasing member 216 are springs, preferably compression springs. The hub 212 may be engageably connected to a proximal end of needle 214, such that displacement or axial translation of the hub 212 causes related motion of the needle 214.

Figure 7:
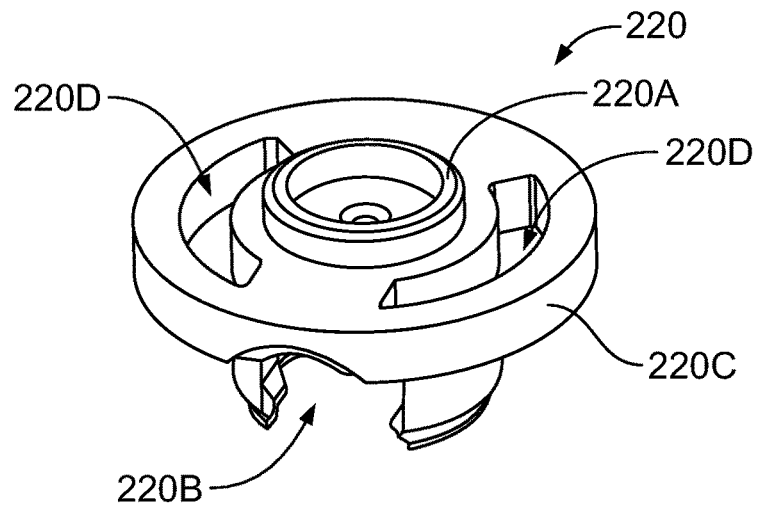
FIG. 7 is an isometric view of a manifold guide according to at least one embodiment of the present invention.

The manifold guide 220, shown in FIG. 7, may include an upper protrusion 220A and a lower chamber 220B separated by a manifold guide ring 220C. Upper protrusion 220A is configured to engage manifold 240. Manifold guide ring 220C is configured to be supported by lockout pins 208 in an initial, locked stage of operation.

As used herein, "needle" is intended to refer to a variety of needles including but not limited to conventional hollow needles, such as a rigid hollow steel needles, and solid core needles more commonly referred to as a "trocars." The needle 214 may include at least one side port 214A for admitting fluid into the hollow interior thereof. While one such side port 214A is illustrated, it will be appreciated that a plurality of side ports may be provided for admitting fluid into the hollow interior of the needle 214. The needle may be any size needle suitable for the type of drug and drug administration (e.g., subcutaneous, intramuscular, intradermal, etc.) intended.

Upon assembly, the proximal end of needle 214 is maintained in fixed contact with hub 212; the proximal end of the needle may be filled with a plug (e.g., a plastic plug, a plug of bonding agent) or may be encapsulated within hub 212. By plugging the proximal end of needle 214 fluid is prevented from flowing out of the needle in this direction during drug delivery. The remainder of needle 214 is permitted to pass through retraction biasing member 216, an aperture 218C of clip 218, clip retainer 219, and manifold guide 220. The needle 214 may further pass through septa 230, manifold body 240B through manifold header 242, sterile boot 250, and base 252 through base opening 252A. Septa 230 and manifold body 240B may reside within lower chamber 220B of manifold guide 220 and within sterile boot 250 until operation of the insertion mechanism. Similarly, septum 230A resides substantially fixed and in sealed engagement within the upper portion of the manifold body 240B and septum 230B resides substantially fixed and in sealed engagement within the lower portion of the manifold body 240B to maintain the sterility of the manifold header 242. Upon insertion of needle 214 into the target, port 214A is located within manifold 220 between the upper and lower septa. This allows fluid to pass into the needle for delivery into the target.

Sterile boot 250 is a collapsible or compressible sterile membrane that is in fixed engagement at a proximal end with the manifold 240 and at a distal end with the base 252. In at least on embodiment, the sterile boot 250 is maintained in fixed engagement at a distal end between base 252 and insertion mechanism housing 202, as shown in FIGS. 10C, 11C, and 12C. Base 252 includes a base opening 252A through which the needle may pass through during operation of the insertion mechanism, as will be described further below. Sterility of the needle is maintained by their initial positioning within the sterile portions of the insertion mechanism. Specifically, as described above, needle 214 is maintained in the sterile environment of the manifold header 242 and sterile boot 250. The base opening 252A of base 252 may be closed from non-sterile environments as well, such as by for example a sealing membrane 254.

Figure 9:
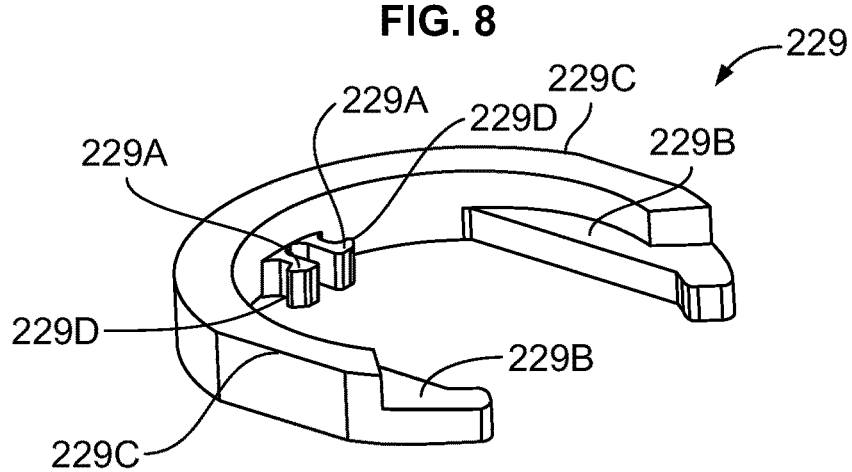
FIG. 9 is an isometric view of a travel limiter according to at least one embodiment of the present invention.

FIG. 9 shows a travel limiter 229, according to at least one embodiment of the present invention. Travel limiter 229 includes prongs 229A and arms 229C. Travel limiter 229 is configured to engage housing 202 such that arms 229C are at least partially disposed within one or more lower circumferential slots 202F of housing 202. Prongs 229A are configured to engage aperture 202E of housing 202. Prongs 229A flex inward during insertion through aperture 202E due to interference with the walls of aperture 202E. After protrusions 229D fully pass through aperture 202E prongs 229A flex outward, thereafter substantially fixing travel limiter 229 in place with respect to housing 202. One or more proximal faces 229B are used to restrict the movement of manifold guide 220 and/or clip retainer 219 as will be described in more detail hereinafter.

Figure 10A:
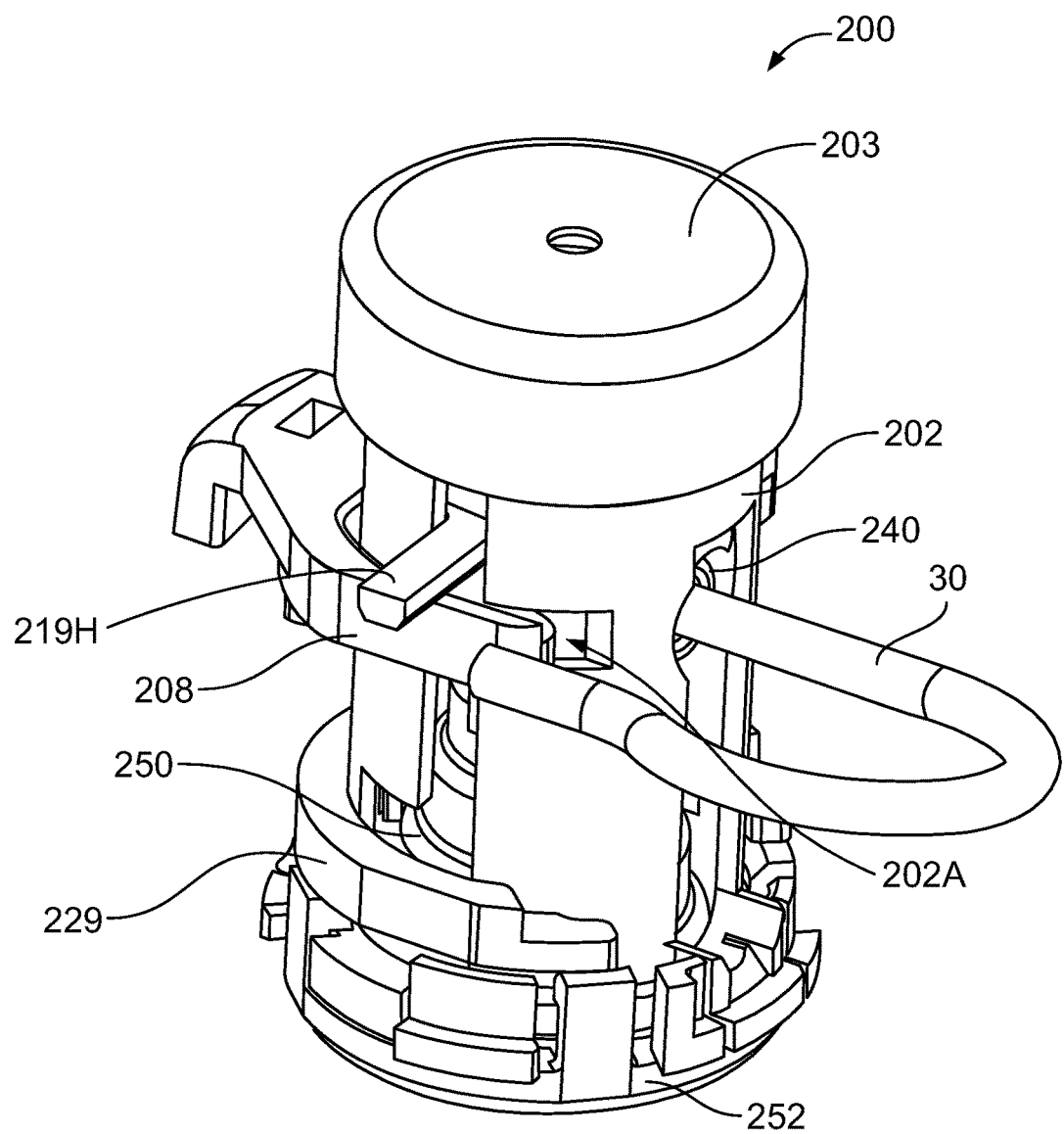
FIG. 10A is an isometric view of a needle insertion mechanism in an initial configuration or initial locked configuration according to at least one embodiment of the present invention.
Figure 10B:
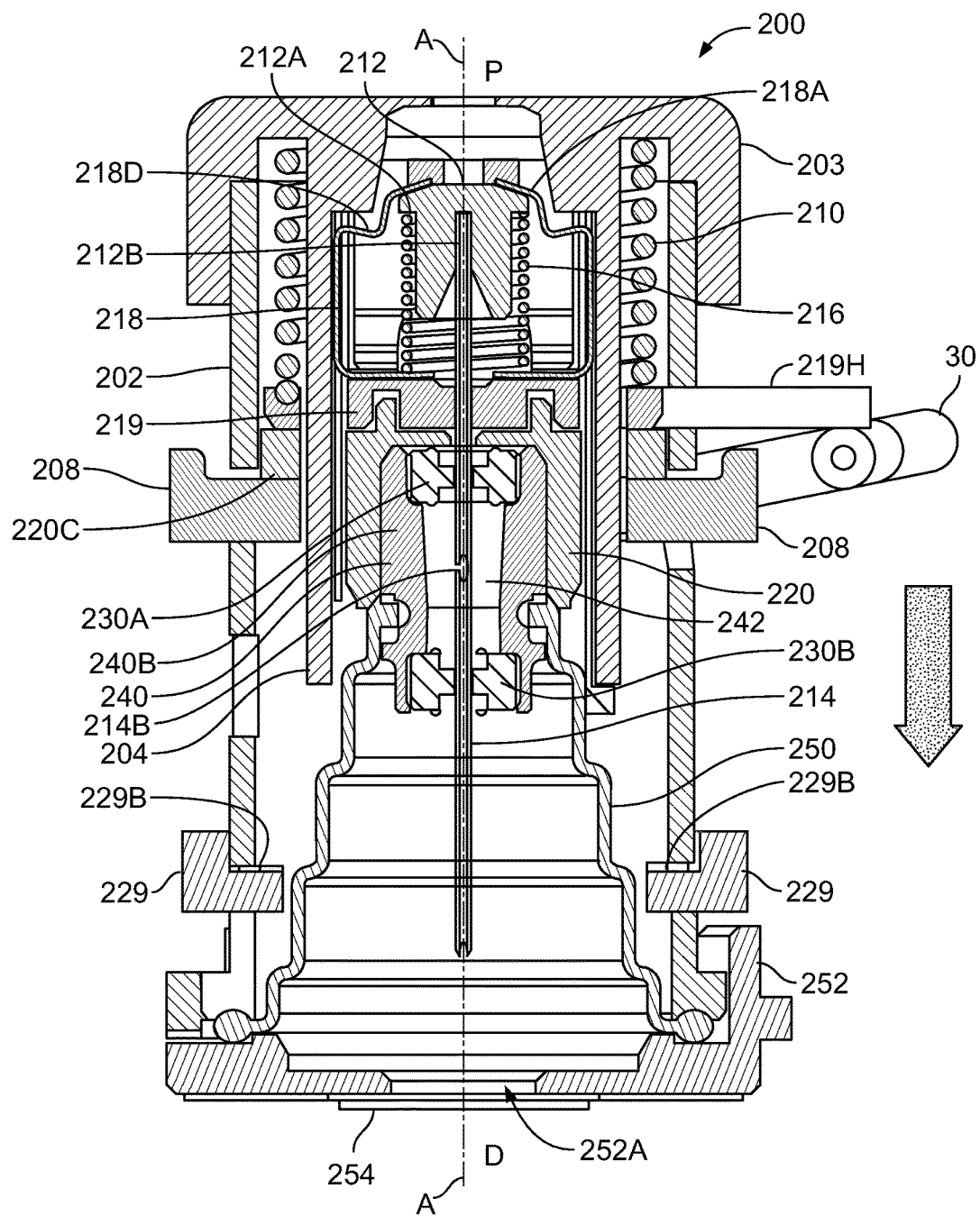
FIG. 10B is a cross-sectional view of the needle insertion mechanism of FIG. 10A.

The operation of the insertion mechanism is described herein with reference to the above components, in view of FIGS. 10-12. FIG. 10A shows an isometric view and FIG. 10B shows a cross-sectional view of the insertion mechanism, according to at least one embodiment of the present invention, in a locked and ready to use stage. Lockout pin(s) 208 are initially positioned within lockout windows 202A of insertion mechanism housing 202. In this initial position, manifold guide ring 220C of manifold guide 220, clip retainer, 219, clip 218, and hub 212 are retained above lockout windows 202A and locking pin(s) 208. In this initial configuration, insertion biasing member 210 and retraction biasing member 216 are each retained in their compressed, energized states. Protrusion 219H is located within slot 202B of housing 202.

As shown in FIG. 1B, the lockout pin(s) 208 (not visible) may be directly displaced by user depression of the activation mechanism 14. As the user disengages any safety mechanisms, such as an optional sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member 210 to decompress and/or de-energize from its initial compressed, energized state.

As shown in FIG. 10B, hub ledges 212A maintain retraction biasing member 216 in a compressed, energized state between hub 212 and clip retainer 219 within chamber 219B. The hub 212 fixedly engages proximal end of needle 214 at hub recess 212B, positioning the hub 212 and needle 214 in an initial position. Prior to operation, sealing member 254 may be removed from bottom of base 252 and base 252 is placed in contact with the target injection site on the target. As lockout pin(s) 208 are displaced by the activation mechanism, as described above, and insertion biasing member 210 is permitted to expand axially in the distal direction (i.e., in the direction of the solid arrow in FIG. 10B), flange 219E is forced by the decompression and/or de-energizing of the insertion biasing member 210 to translate axially in the distal direction to insert the needle 214 into the target. The axial translation of the clip retainer and manifold guide is directed, and maintained in rotational alignment, by interaction between the guide protrusions 204 of the insertion mechanism housing cap 203 and corresponding pass-throughs 219D and 220D of the clip retainer 219 and manifold guide 220. Release surfaces 218A of clip 218 engage hub 212 and retain the refraction biasing member 216 in a compressed, energized state while the manifold guide 220 travels axially in the distal direction.

Figure 11A:
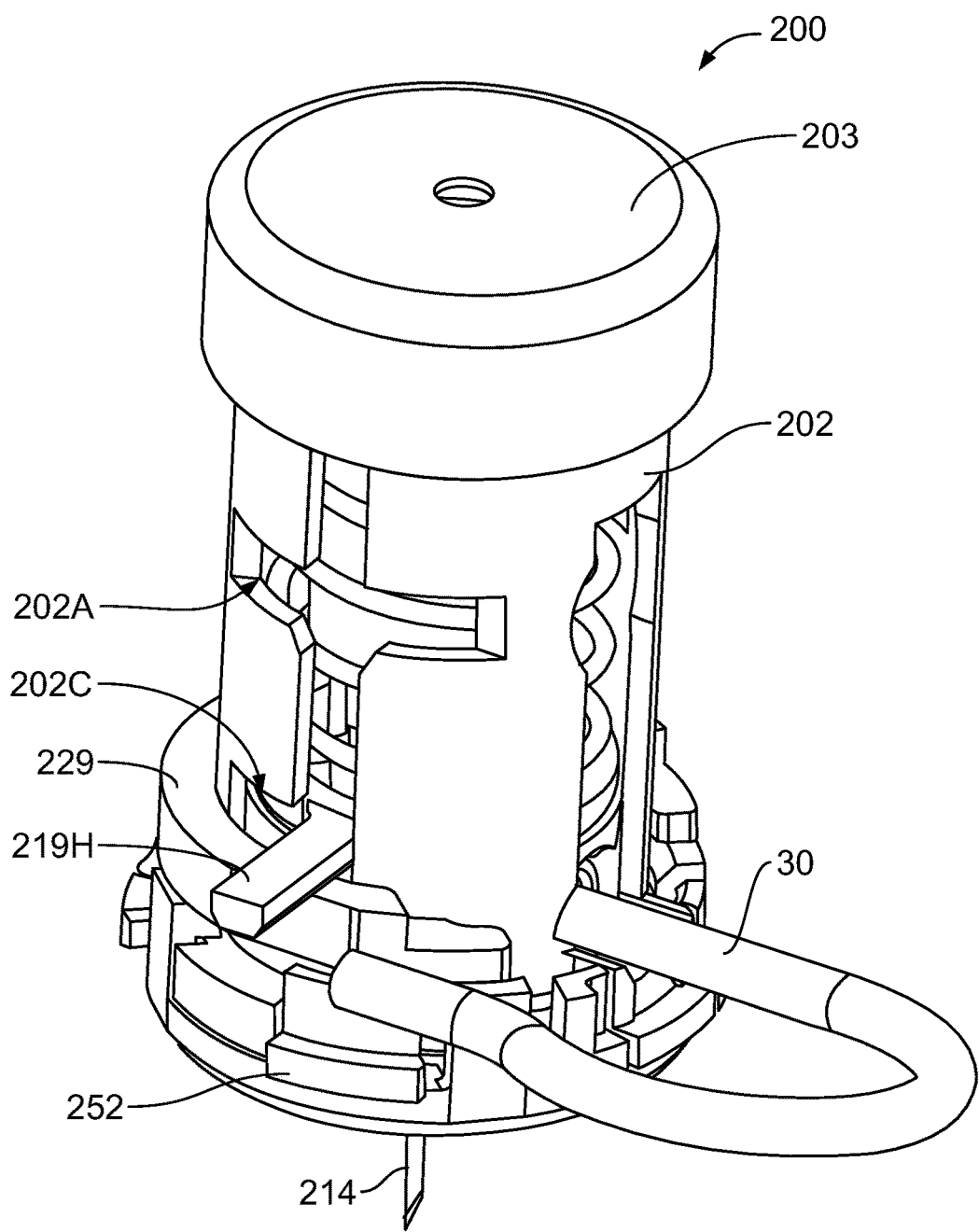
FIG. 11A is an isometric view of the needle insertion mechanism of FIG. 10A in an administration configuration.
Figure 11B:
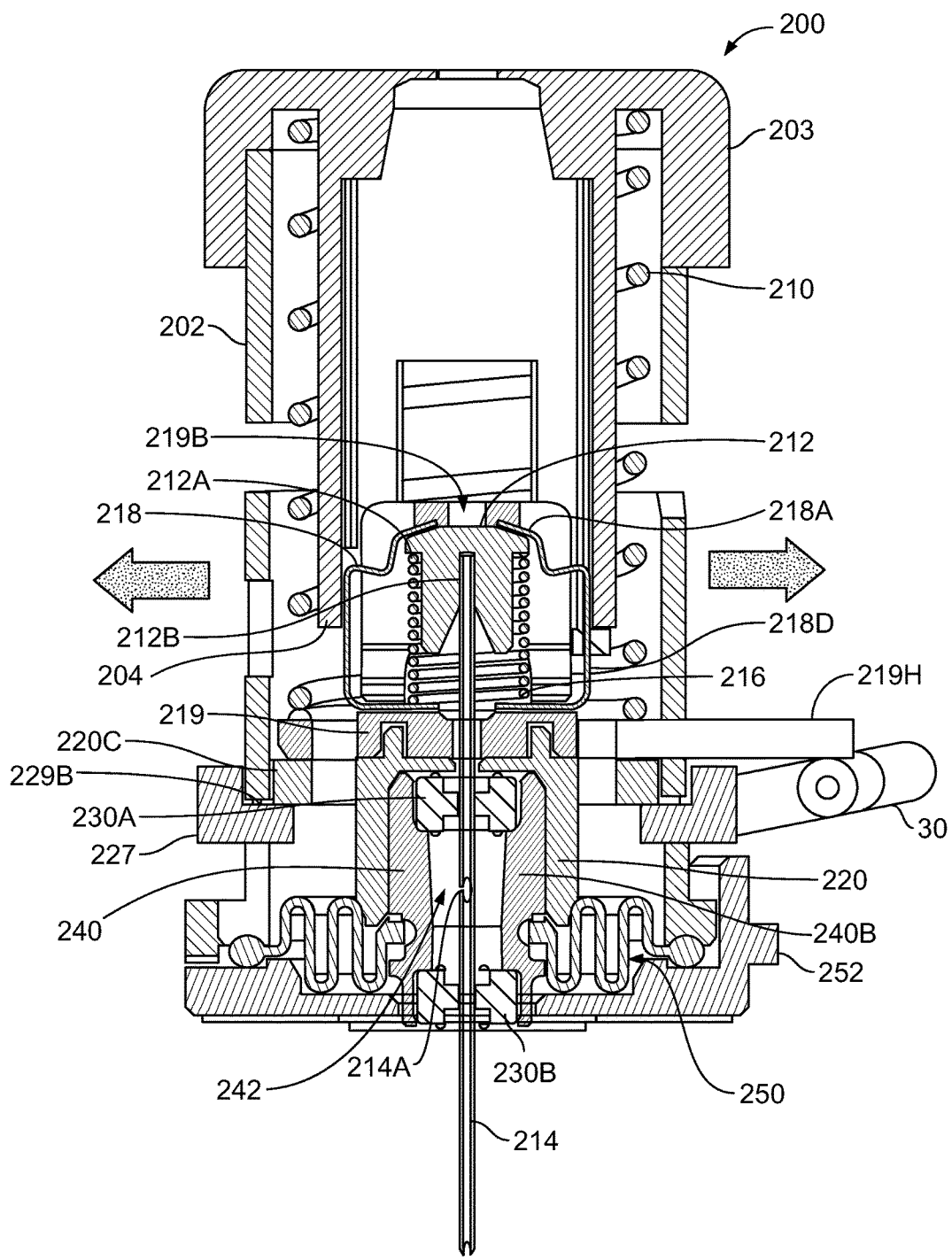
FIG. 11B is a cross-sectional view of the needle insertion mechanism of FIG. 10A in an administration configuration.

FIG. 11A shows an isometric and FIG. 11B shows a cross-sectional view of an insertion mechanism in an administration configuration, that is, with the needle 214 and hub 212 in an administration position. In this position, manifold guide 220 is in contact with proximal surfaces 229B of travel limiter 229. As shown, sterile boot 250 is permitted to collapse as the insertion biasing member 210 expands and inserts the needle 214 into the target. At this stage, shown in FIG. 11, needle 214 is introduced into the target for drug delivery. As the fluid pathway connection is made to the drug container and the drive mechanism is activated, the fluid drug treatment is forced from the drug container through the fluid pathway connection and the sterile fluid conduit into the manifold header 242 and through the needle 214 for delivery into the target. Accordingly, activation of the insertion mechanism inserts the needle 214 into a target or the target placing the fluid pathway in communication with the target. As can be seen in FIG. 11B arms 218D are flexed inward due to contact with guide protrusions 204. Hence, release surfaces 218A maintain contact with hub 212 and prevent refraction biasing member 216 from decompressing or de-energizing.

Figure 12A:
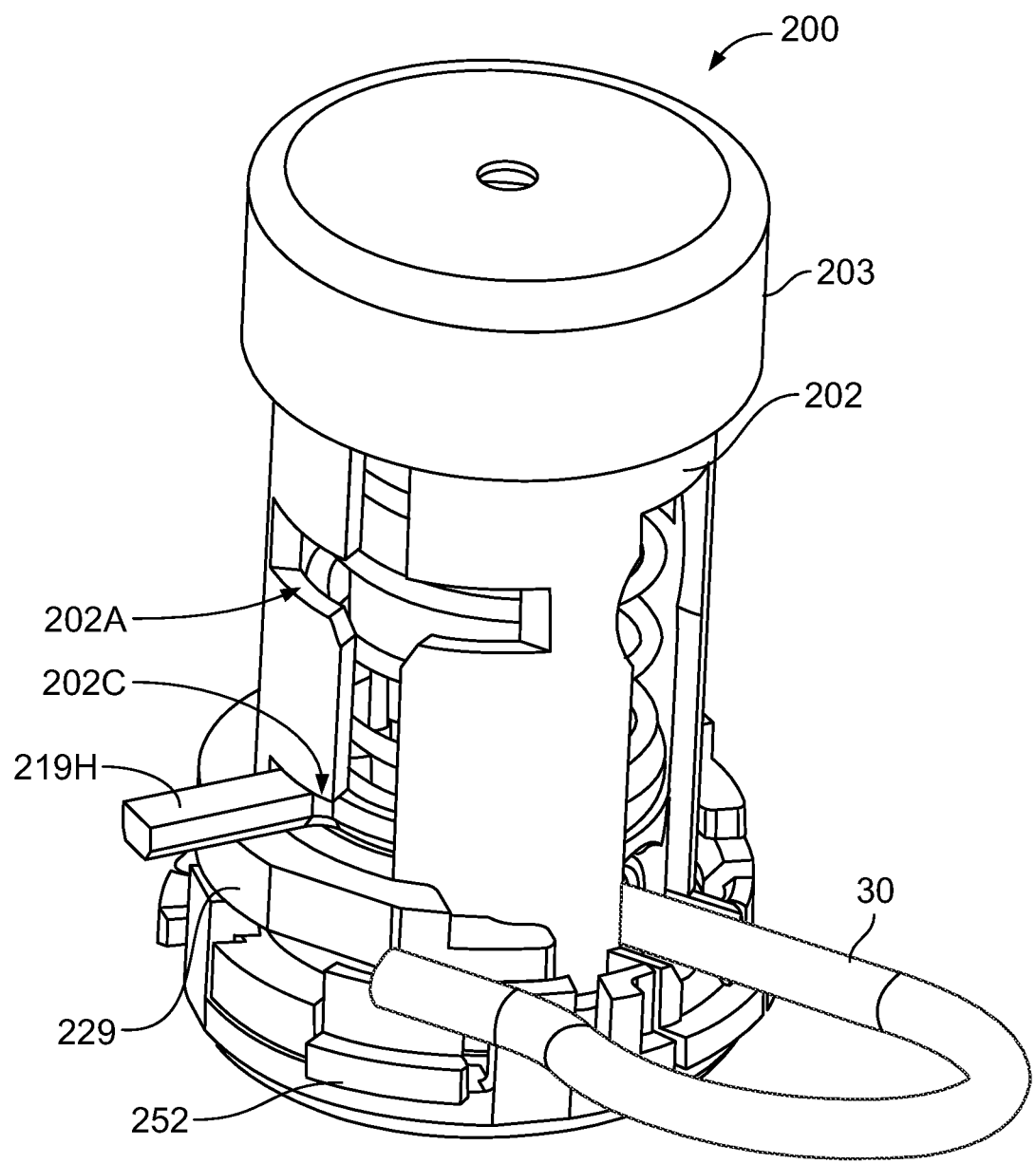
FIG. 12A is an isometric view of the needle insertion mechanism of FIG. 10A in a retracted configuration or unlocked configuration.
Figure 12B:
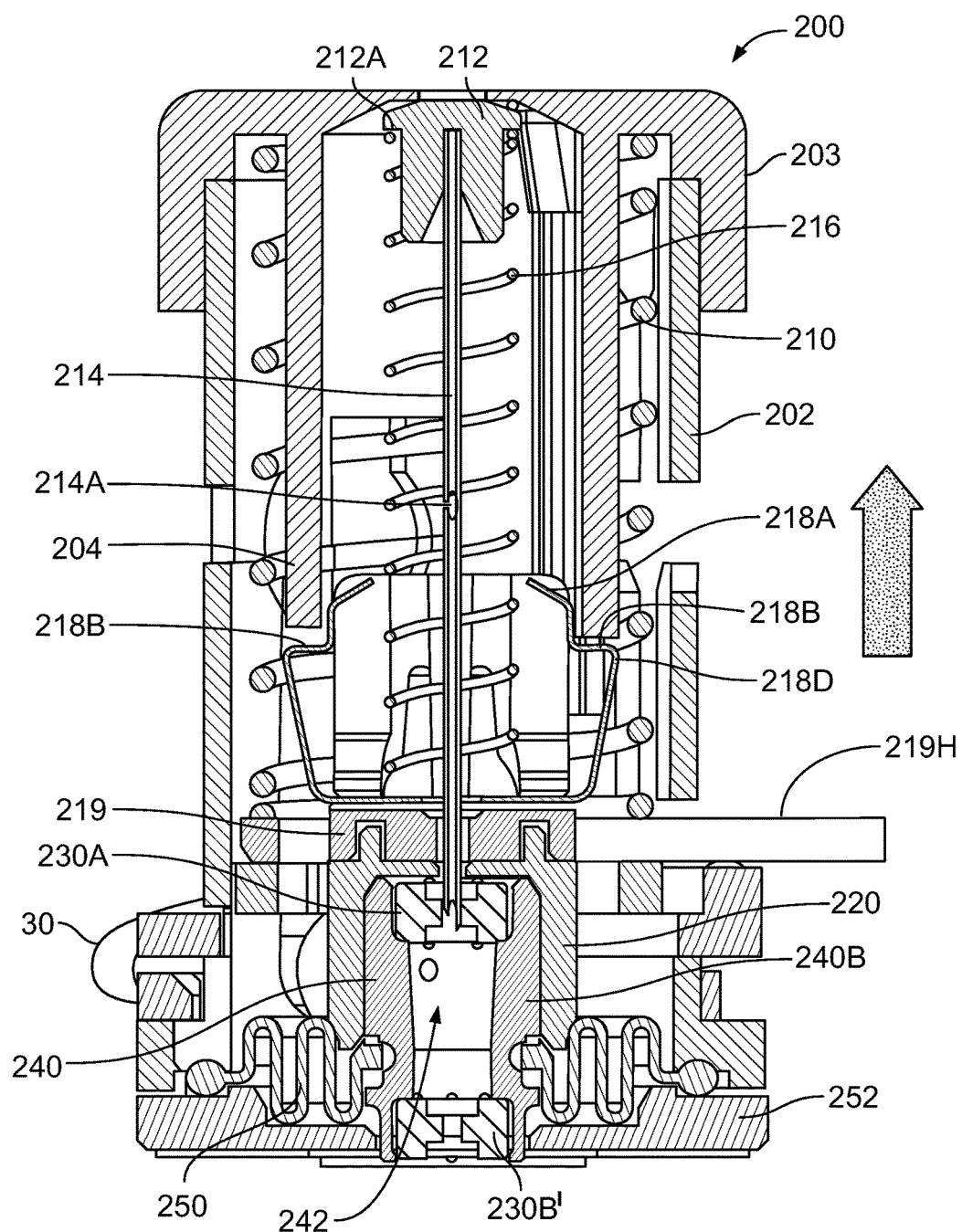
FIG. 12B is a cross-sectional view of the needle insertion mechanism of FIG. 12A in a retracted configuration or unlocked configuration.

As shown in FIG. 12A-12B, needle 214 is retracted back (i.e., axially translated in the proximal direction) into the insertion mechanism housing 202. FIG. 12A shows an isometric view of the insertion mechanism in this configuration and FIG. 12B shows a cross-sectional view. The plane of cross-section in FIG. 12B is not the same as that of FIG. 10B and FIG. 11B but is rotated with respect to the cross-sectional plane of those views. This retraction may be triggered by user activation, automatic retraction at completion of dose delivery, failure or fault of the drive mechanism, or upon activation by one or more sensors. Upon full distal displacement of insertion biasing member 210, protrusion 219H is substantially aligned with circumferential slot 202C of housing 202 and arms 218D are constrained by guide protrusions 204 as shown in FIGS. 11A-11B (position A). In this position clip retainer 219 is able to rotate with respect to housing 202, housing cap 203, and guide protrusions 204 to a position B as shown in FIGS. 12A-B. The rotation of clip retainer 219 is transmitted to clip 218. In position B, arms 218D of clip 218 are no longer restrained by guide protrusions 204, hence, arms 218D flex radially outward (i.e., in the direction of the hollow arrows shown in FIG. 11B) due to their outward bias. This causes release surfaces 218A to disengage from hub 212. Upon disengagement of the release surfaces 218A from hub 212, retraction biasing member 216 is permitted to expand axially in the proximal direction (i.e., in the direction of hatched arrow in FIG. 12B) from its initial compressed, energized state. The clip 218 is prevented from retracting or axial translation in the proximal direction by contact between the lockout surfaces 218B and the distal ends of the guide protrusions 204, as shown in FIG. 12B. This lockout also prevents axial translation in the proximal direction of the clip retainer 219, manifold guide 220 and insertion mechanism components that are distal to (i.e., below) the manifold guide ring 220C. In this configuration, needle 214 is no longer exposed, therefore making pump 10 safe to handle.

Figure 13A:
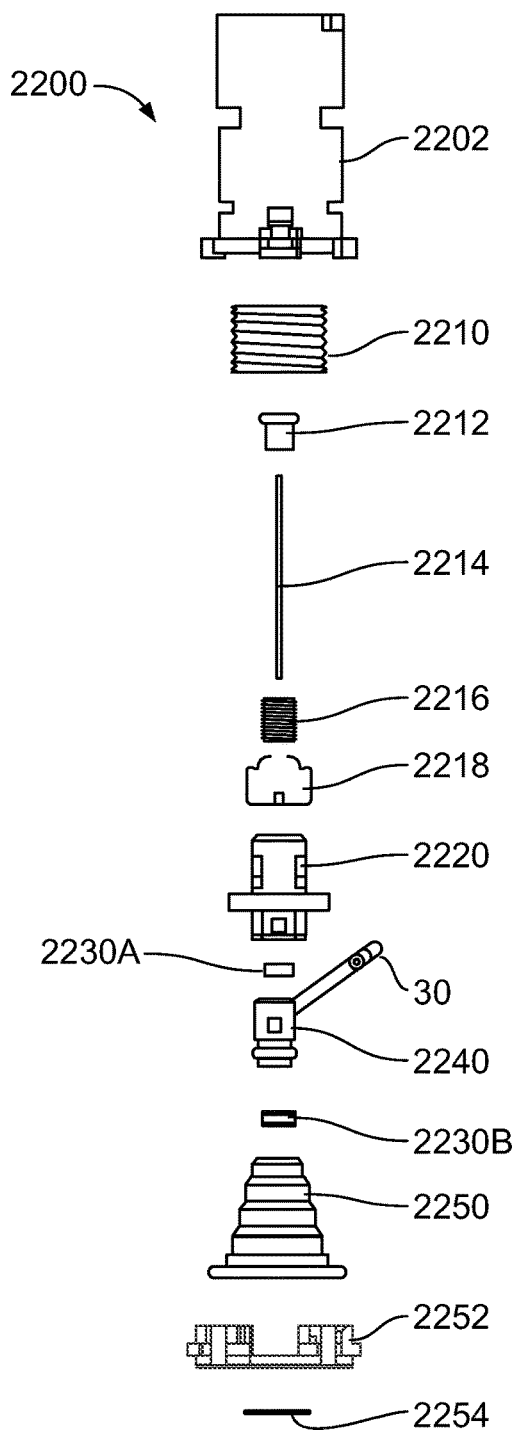
FIG. 13A is an exploded view of an insertion mechanism, according to a second embodiment of the invention.
Figure 13B:
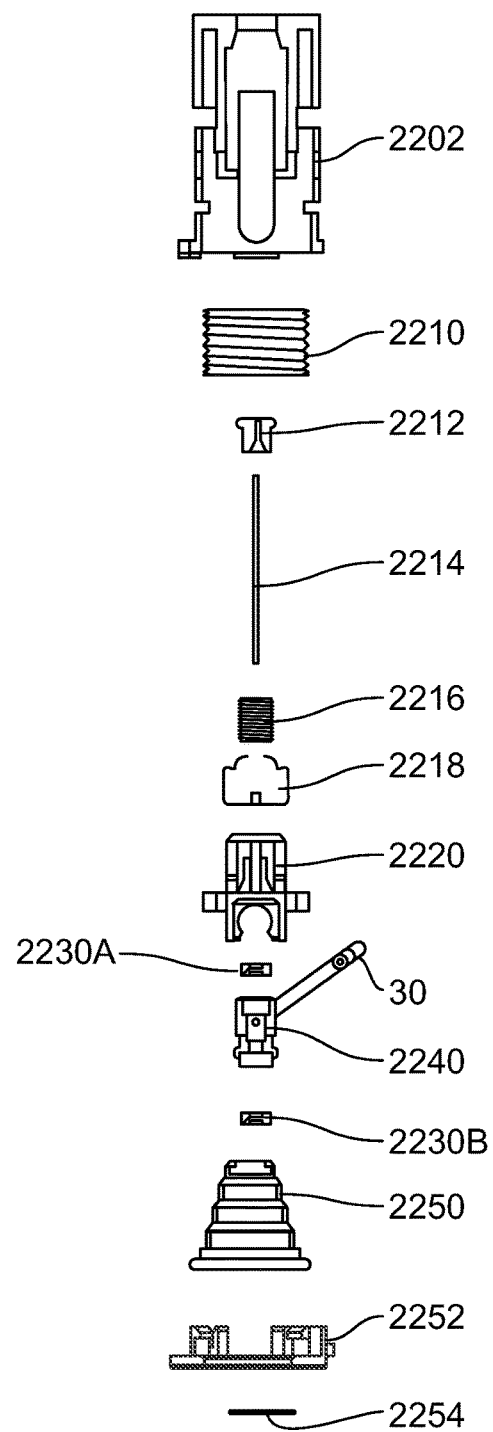
FIG. 13B is a cross-sectional exploded view of the insertion mechanism of FIG. 13A.

In a second embodiment, shown in FIG. 13, the insertion mechanism 2200 includes an insertion mechanism housing 2202, a base 2252, and a sterile boot 2250, as shown in FIGS. 13A and 13B. Base 2252 may be connected to assembly platform 20 to integrate the insertion mechanism into the drug pump 10 (as shown in FIG. 1B). The connection of the base 2252 to the assembly platform 20 may be, for example, such that the bottom of the base is permitted to pass through a hole in the assembly platform to permit direct contact of the base to the target. In such configurations, the bottom of the base 2252 may include a sealing membrane 2254 that, at least in one embodiment, is removable prior to use of the drug pump 10. Alternatively, the sealing membrane 2254 may remain attached to the bottom of the base 2252 such that the needle 2214 pierces the sealing membrane 2254 during operation of the drug pump 10. As shown in FIGS. 13A and 13B, the insertion mechanism 2200 may further include an insertion biasing member 2210, a hub 2212, a needle 2214, a retraction biasing member 2216, a clip 2218, a manifold guide 2220, a travel limiter 2229, and a manifold 2240 including a manifold body 2240B, septa 2230A and 2230B. The manifold 2240 may connect to sterile fluid conduit 30 to permit fluid flow through the manifold 2240, needle 2214, and into the target during drug delivery, as will be described in further detail herein.

As shown in FIG. 14, insertion mechanism housing 2202 may be a substantially cylindrical component having an inner chamber within which the components of the insertion mechanism are substantially housed. Housing 2202 may further include axial slot 2202D within which sterile fluid conduit 30 may translate during needle insertion as will be described hereinafter. Housing 202 further includes one or more lockout windows 2202A which are configured to engage lockout pins 208 in an initial, locked configuration. Lockout pins 208 may pass through windows 2202A to the interior of housing 2202 such that manifold guide ring 2220C may rest upon lockout pins 208 in an initial, locked configuration. Housing 2202 may additionally include limiter slots 2202F which are configured to accept and engage travel limiter 2229.

Housing 2202 may additionally include guide protrusions 2204. Guide protrusions 2204 may, alternatively, be a portion of a separate component located within housing 2202. The guide protrusions 2204 slidably engage manifold guide 2220 at pass-throughs 2220D on manifold guide ring 2220C. The insertion biasing member 2210 initially resides in an energized state between the guide protrusions 2204 and inner surface of insertion mechanism housing 2202 and between the interior proximal end of the insertion mechanism housing 2202 and the manifold guide ring 2220C. Therefore upon activation by the user, as described further hereinafter, the insertion biasing member 2210 is caused to bear against and exert force upon manifold guide ring 2220C as the insertion biasing member 2210 decompresses and/or de-energizes, causing axial translation in the distal direction of the manifold guide 2220 and the components retained within manifold guide 2220. Prior to activation, the insertion biasing member 2210 is maintained substantially above locking windows 2202A in a compressed, energized state.

The manifold guide 2220, shown in FIG. 15, may include an upper, clip retainer or clip retaining portion 2219 and a lower chamber 2220B separated by a guide ring 2220C. The clip retainer or clip retaining portion 2219 may include a clip interface slot 2219A for engageable retention of clip 2218. Flexible extensions 2219G may be configured to flex outward during installation of clip 2218 into clip interface slot 2219A and, upon clip insertion, return to their natural positions. Hence, the clip 2218 is substantially retained in axial position with respect to manifold guide 2220. The clip retainer or clip retaining portion 2219 may have an inner chamber 2219B, within which the retraction biasing member 2216, the clip 2218, and the hub 2212 may reside during an initial locked stage of operation, and an outer upper chamber 2219C, which interfaces with the insertion biasing member 2210. In at least one embodiment, the insertion biasing member 2210 and the retraction biasing member 2216 are springs, preferably compression springs. The hub 2212 may be engageably connected to a proximal end of needle 2214, such that displacement or axial translation of the hub 2212 causes related motion of the needle 2214. Manifold guide ring 2220C is configured to be supported by lockout pins 208 in an initial, locked stage of operation.

Travel limiter 2229, shown in FIG. 16, may be configured to include a living hinge 2229D which allows arms 2229C of travel limiter 2229 to transform from a "closed" position in which proximal faces 2229B restrict axial movement of manifold guide 2220 to an "open" position in which travel limiter 2229 allows additional axial movement of manifold guide 2220, thereby allowing needle retraction. Travel limiter 2229 is configured to be at least partially within the interior of housing 2202 in an initial, installed configuration. After transformation to its "open" position travel limiter 2229 may be positioned substantially outside of housing 2202 or may remain partially within housing 2202 but allow additional distal movement of manifold guide 2220. Alternatively, transformation from the "closed" position to the "open" position may be performed by translating travel limiter 2229 in a direction perpendicular to axis A such that proximal faces 2229B allow additional movement of manifold guide 2220.

As used herein, "needle" is intended to refer to a variety of needles including but not limited to conventional hollow needles, such as a rigid hollow steel needles, and solid core needles more commonly referred to as a "trocars." The needle may be any size needle suitable for the type of drug and drug administration (e.g., subcutaneous, intramuscular, intradermal, etc.) intended. As with the needle 214 of the first embodiment, the needle 2214 may include at least one side port 2214A for admitting fluid into the hollow interior thereof. While one such side port 2214A is illustrated, it will be appreciated that a plurality of side ports may be provided for admitting fluid into the hollow interior of the needle 2214. Upon assembly, the proximal end of needle 2214 is maintained in fixed contact with hub 2212; the proximal end of the needle may be filled with a plug (e.g., a plastic plug, a plug of bonding agent) or may be encapsulated within hub 2212. By plugging the proximal end of needle 2214 fluid is prevented from flowing out of the needle in this direction during drug delivery. The remainder of needle 2214 is permitted to pass through retraction biasing member 2216, an aperture 2218C of clip 2218 and manifold guide 2220. The needle 2214 may further pass through septa 2230, manifold body 2240B through manifold header 2242, sterile boot 2250, and base 2252 through base opening 2252A. Septa 2230 and manifold body 2240B may reside within lower chamber 2220B of manifold guide 2220 and within sterile boot 2250 until operation of the insertion mechanism. Similarly, septum 2230A resides substantially fixed and in sealed engagement within the upper portion of the manifold body 2240B and septum 2230B resides substantially fixed and in sealed engagement within the lower portion of the manifold body 2240B to maintain the sterility of the manifold header 2242. Upon insertion of needle 2214 into the target, port 2214A is located within manifold 2220 between the upper and lower septa. This allows fluid to pass into the needle 2214 for delivery into the target.

Figure 17A:
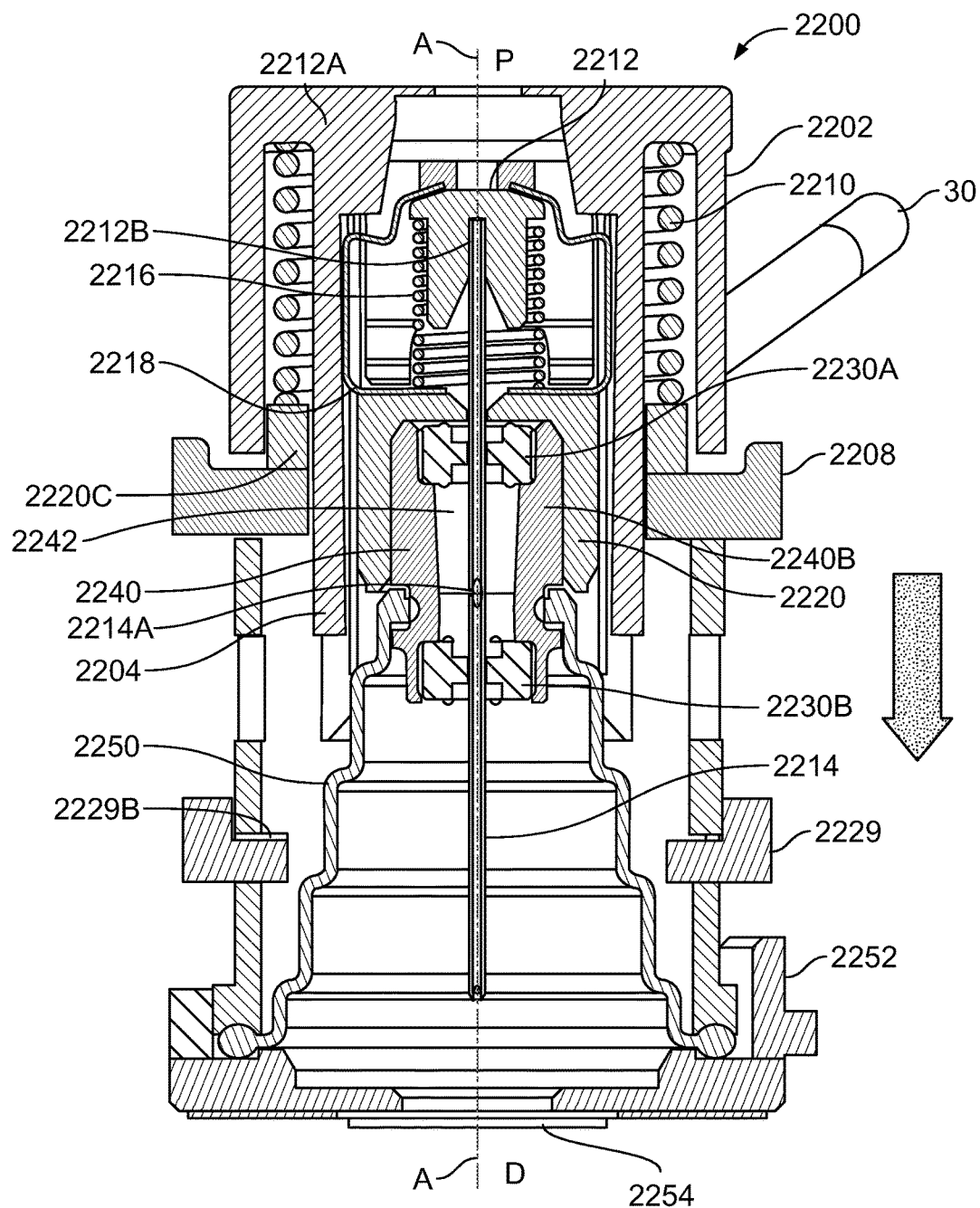
FIG. 17A is a cross-sectional view of a needle insertion mechanism in an initial configuration or initial locked configuration according to at least one embodiment of the present invention.
Figure 17B:
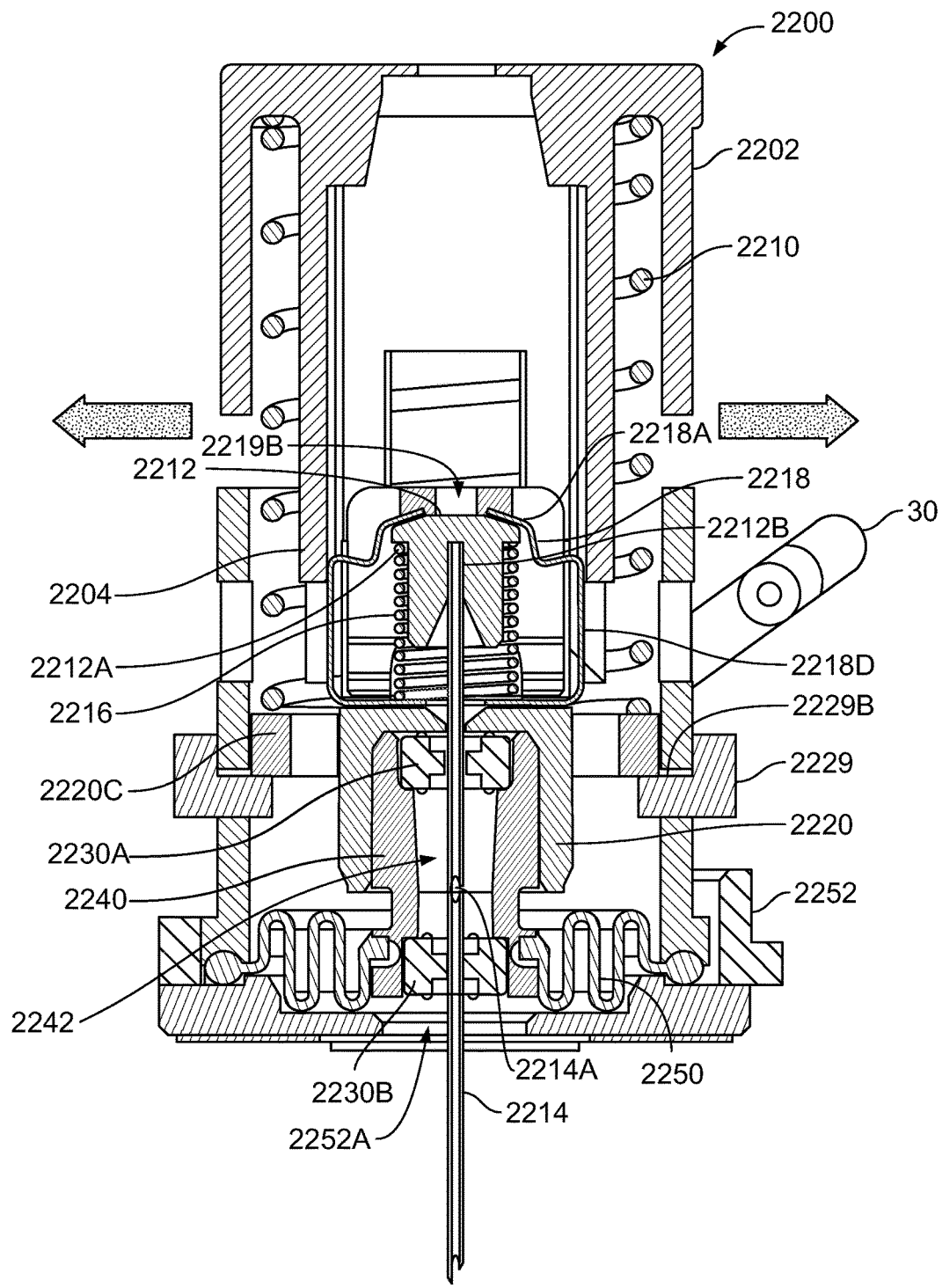
FIG. 17B is a cross-sectional view of the needle insertion mechanism of FIG. 17A in an administration configuration.
Figure 17C:
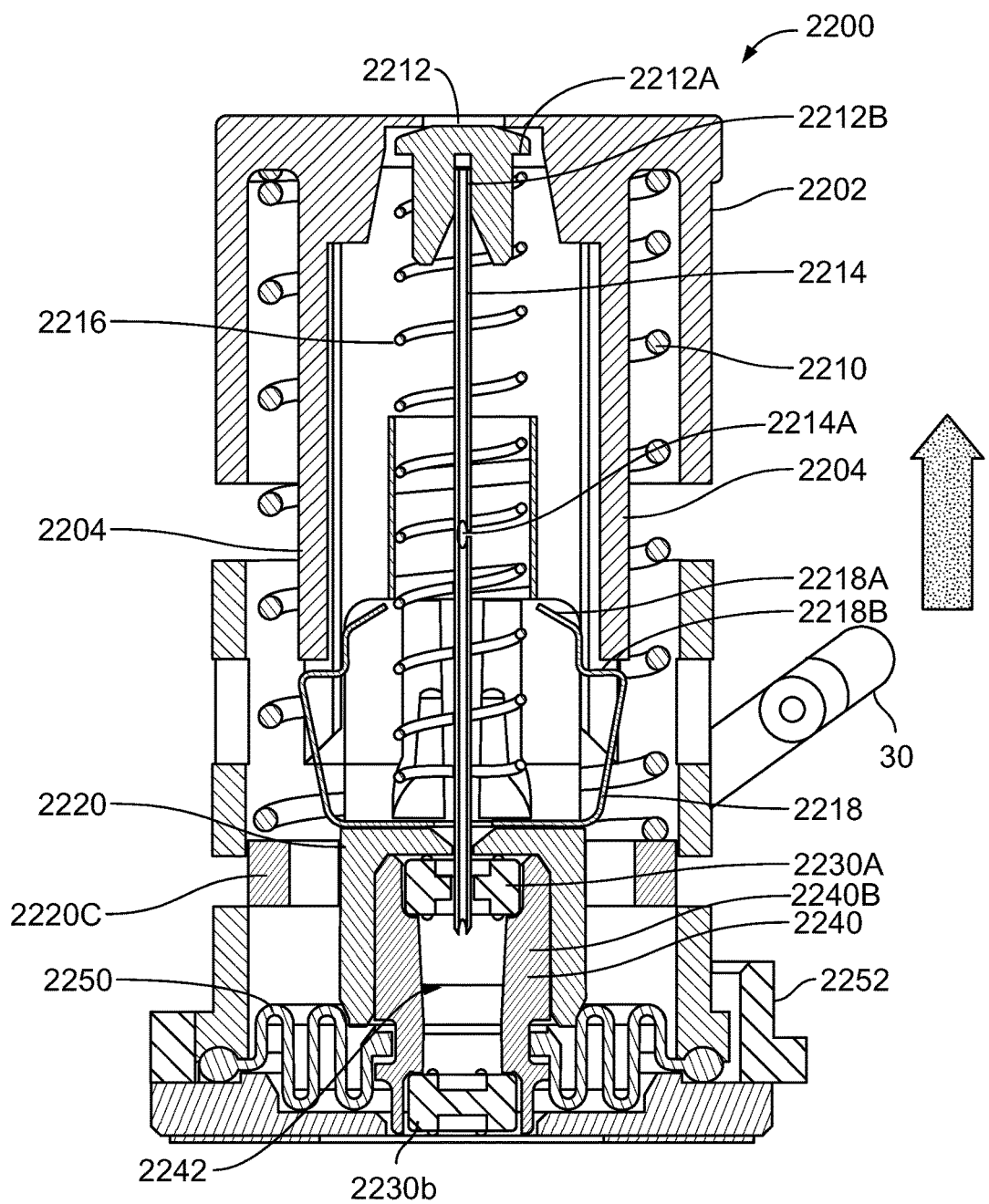
FIG. 17C is a cross-sectional view of the needle insertion mechanism of FIG. 17A in a retracted configuration or unlocked configuration.

Sterile boot 2250 is a collapsible or compressible sterile membrane that is in fixed engagement at a proximal end with the manifold 2240 and at a distal end with the base 2252. In at least on embodiment, the sterile boot 2250 is maintained in fixed engagement at a distal end between base 2252 and insertion mechanism housing 2202, as shown in FIGS. 17A-C. Base 2252 includes a base opening 2252A through which the needle may pass through during operation of the insertion mechanism, as will be described further below. Sterility of the needle is maintained by its initial positioning within the sterile portions of the insertion mechanism. Specifically, as described above, needle 2214 is maintained in the sterile environment of the manifold header 2242 and sterile boot 2250. The base opening 2252A of base 2252 may be closed from non-sterile environments as well, such as by for example a sealing membrane 2254.

The operation of one embodiment of the insertion mechanism is described herein with reference to the above components, in view of FIGS. 17A-C. FIG. 17A shows a cross-sectional view of the insertion mechanism, according to at least one embodiment of the present invention, in a locked and ready to use stage. Lockout pin(s) 2208 are initially positioned within lockout windows 2202A of insertion mechanism housing 2202. In this initial position, manifold guide ring 2220C of manifold guide 2220, clip 2218, and hub 2212 are retained above lockout windows 2202A and locking pin(s) 2208. In this initial configuration, insertion biasing member 2210 and retraction biasing member 2216 are each retained in their compressed, energized states.

As shown in FIG. 1B, the lockout pin(s) 2208 (not visible) may be directly displaced by user depression of the activation mechanism 14. As the user disengages any safety mechanisms, such as an optional sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 2202A of insertion mechanism housing 2202. Displacement of the lockout pin(s) 2208 permits insertion biasing member 2210 to decompress and/or de-energize from its initial compressed, energized state.

As shown in FIG. 17B, hub ledges 2212A maintain retraction biasing member 2216 in a compressed, energized state between hub 2212 and manifold guide 2220 within chamber 2219B. The hub 2212 fixedly engages proximal end of needle 2214 at hub recess 2212B. Prior to operation, sealing member 2254 may be removed from bottom of base 2252 and base 2252 is placed in contact with the target injection site on the target. As lockout pin(s) 2208 are displaced by the activation mechanism, as described above, and insertion biasing member 2210 is permitted to expand axially in the distal direction (i.e., in the direction of the solid arrow in FIG. 17A), guide ring 2220C is forced by the decompression and/or de-energizing of the insertion biasing member 2210 to translate axially in the distal direction to insert the needle 2214 into a target. The axial translation of the manifold guide is directed, and maintained in rotational alignment by interaction between the guide protrusions 2204 of the insertion mechanism housing 2202 and corresponding pass-throughs 2220D of the manifold guide 2220. Release surfaces 2218A of clip 2218 engage hub 2212 and retain the retraction biasing member 2216 in a compressed, energized state while the manifold guide 2220 travels axially in the distal direction. FIG. 17B shows a cross-sectional view of an insertion mechanism according to at least one embodiment in an administration configuration, that is, with the needle 2214 and hub 2212 in an administration position. In this position, manifold guide 2220 is in contact with proximal surfaces 2229B of travel limiter 2229. As shown, sterile boot 2250 is permitted to collapse as the insertion biasing member 2210 expands and inserts the needle 2214 into the target. At this stage, needle 2214 is introduced into the target for drug delivery. As the fluid pathway connection is made to the drug container and the drive mechanism is activated, the fluid drug treatment is forced from the drug container through the fluid pathway connection and the sterile fluid conduit into the manifold header 2242 and through the needle 2214 for delivery into the target. Accordingly, activation of the insertion mechanism inserts the needle 2214 into the target, which may be a tissue, for example, placing the fluid pathway in communication with the target. As can be seen in FIG. 17B arms 2218D are flexed inward due to contact with guide protrusions 2204. Hence, release surfaces 2218A maintain contact with hub 2212 and prevent retraction biasing member 2216 from decompressing or de-energizing.

As shown in FIG. 17C, needle 2214 is retracted back (i.e., axially translated in the proximal direction) into the insertion mechanism housing 2202. This retraction may be triggered by user activation, automatic retraction at completion of dose delivery, failure or fault of the drive mechanism, or upon activation by one or more sensors. To effect retraction of needle 2214, travel limiter 2229 is displaced and/or transformed such that manifold guide ring 2220C is no longer supported by proximal faces 2229B. Hence, further decompression or de-energizing of insertion biasing member 2210 causes manifold guide 2220 to move in the distal direction (direction of solid arrow in FIG. 17A). In this position arms 2218D of clip 2218 are no longer restrained by guide protrusions 2204, hence, arms 2218D flex radially outward (i.e., in the direction of the hollow arrows shown in FIG. 17B) due to their outward bias. This causes release surfaces 2218A to disengage from hub 2212. Upon disengagement of the release surfaces 2218A from hub 2212, retraction biasing member 2216 is permitted to expand axially in the proximal direction (i.e., in the direction of hatched arrow in FIG. 17C) from its initial compressed, energized state. The clip 2218 is prevented from retracting or axial translation in the proximal direction by contact between the lockout surfaces 2218B and the distal ends of the guide protrusions 2204, as shown in FIG. 17C. This lockout also prevents axial translation in the proximal direction of the manifold guide 2220 and insertion mechanism components that are distal to (i.e., below) the manifold guide ring 2220C. In this configuration, needle 2214 is no longer exposed, therefore making pump 10 safe to handle.

Activating retraction of the needle may be accomplished through many mechanisms. For example, a retraction activation mechanism such as a button may be provided on the outside of housing 12 which, when depressed by the user, activates retraction of the needle from the target. For example, in one embodiment, depressing the retraction activation mechanism may cause clip retainer 219 to rotate to position B, hence allowing retraction biasing member 216 to expand and retract needle 214. In another embodiment, depression of the retraction activation mechanism may cause displacement and/or transformation of travel limiter 2229 and allow retraction biasing member 2216 to decompress and retract the needle. Actuation of the retraction activation mechanism may be spring assisted such that the travel and/or force required to depress the retraction activation mechanism is reduced. Alternatively, or additionally, upon drive mechanism 100 reaching end-of-dose an electrical or mechanical actuator may cause activation of retraction. For example, upon end-of-dose, an electrical connection may be made such that a current is applied to a nitinol component. Upon application of the current the nitinol component's temperature rises. Because of the shape-memory characteristics of nitinol, this component may be configured, upon an increase in temperature, to transform from a first configuration to a second configuration. In this second configuration, the nitinol component may allow or cause the actuation of the retraction of the needle by, for example, rotating clip retainer 219 or displacing or transforming travel limiter 2229.

Alternatively, or additionally, a sensor such as sensor 24 may, when drug pump 10 is removed from the target, cause or allow activation of the retraction of the needle. For example, when pump 10 is installed on the target the position of sensor 24 may prevent retraction of the needle. Upon removal from the target a change in configuration of sensor 24 may allow retraction. In another embodiment, a light sensor may be placed on drug pump 10 near to base opening 252. When drug pump 10 is in place on the target, light would be substantially blocked from entering the light sensor. Upon removal of drug pump 10 from the target, light may be sensed by the light sensor and the light sensor may trigger an electromechanical actuator to allow or cause activation of retraction. In other embodiments, a pin-type press-fit interconnect is used to initiate retraction of the needle. The pin may be biased to at least partially protrude from housing 12 and be displaced upon placement of pump 10 on the target. When displaced, the pin may engage a female hole on a PCB which may be a part of power and control system 400. Upon removal of pump 10 from the target, the biased pin disengages the female PCB hole, thereby causing a signal to activate the retraction of the needle.

Further, the insertion mechanism may be configured such that existence or detection of an unsafe condition, such as displacement of the insertion mechanism with respect to housing 12 or platform 20, causes actuation of the retraction of the needle. For example, upon removal of locking pins 208 from the lockout windows, the needle insertion mechanism may be free to float in a distal direction relative to housing 12 and/or platform 20. A biasing member may be used such that the needle insertion mechanism is biased to move in a distal direction with respect to housing 12 and/or platform 20. However, when pump 10 is in place on a target, motion is restrained by the target. Upon removal of pump 10 from the target, the biasing member may decompress or de-energize and cause the needle insertion mechanism to move distally with respect to housing 12 and/or platform 20. This distal displacement may cause or allow the activation of retraction. Alternatively, or additionally, adhesive may be located on the distal face of the needle insertion mechanism which resists removal from the target and causes the needle insertion mechanism to move distally with respect to the housing 12 or platform 20. The safety to the user may be enhanced through the use of one or more of these mechanisms for needle retraction. For example, if drug pump 10 is inadvertently removed from the target after needle insertion, the automatic retraction of the needle by one of the means described above reduces the risk of a needle-stick injury.

Figure 18:
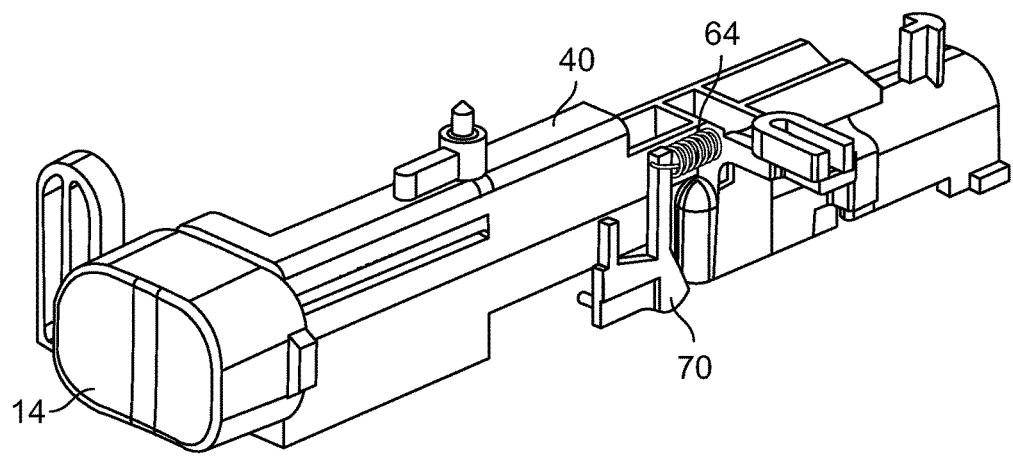
FIG. 18 is an isometric view of a needle retraction release mechanism of at least one embodiment of the present invention.
Figure 19:
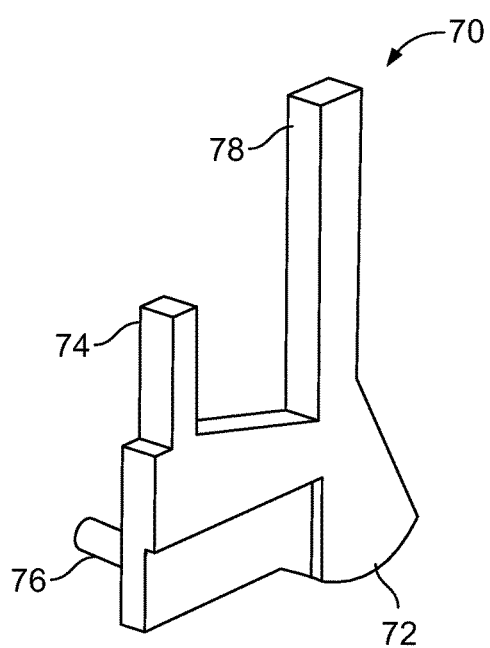
FIG. 19 is an isometric view of a pivot of at least one embodiment of the present invention.

FIG. 18 shows one embodiment of a retraction activation mechanism. Retraction activation biasing member 64 is connected at the one end to control arm 40 and at the other end to connection arm 78 of pivot 70. Target contact portion 72 of pivot 70 may extend through lower housing 12B and its motion may be restrained by contact with the target when pump 10 is installed on the target. Pin 76 of pivot 70 is configured to engage housing 12 or another component of the pump, thereby allowing rotation of pivot 70 about pin 76. Extension 74 of pivot 70 is configured to contact protrusion 219H during operation. Depression of activation mechanism 14 by the user causes displacement of slide 40, which activates the drug pump to insert the needle into the target by transforming lockout pins 208; depression of the activation mechanism 14 may also activate the drug pump to perform additional actions. Displacement of control arm 40 displaces the first end of retraction activation biasing member 64, displacement of the second end of retraction activation biasing member is resisted by pivot 70 due to contact between target contact portion 72 of pivot 70 with the target. Upon removal of drug pump 10 from the target, pivot 70 is permitted to rotate and is caused to rotate by the energy stored in retraction activation biasing member 64. As pivot 70 rotates, extension 74 contacts protrusion 219H and imparts rotation to clip retainer 219, thereby causing or allowing retraction of the needle from the target.

Retraction of the needle may further be initiated upon a failure and/or fault of drive mechanism 100. For example, the drive mechanism may include a tether which serves to meter or control the rate of delivery of the contents of drug container 50. The tension applied to, or sustained by, the tether may be monitored by one or more sensors. A reduction in the tension of the tether may be an indication that the tether is not properly metering or controlling the delivery of the medicament. The sensor may be a mechanical component or linkage which is in contact with a portion of the tether, the contact at least partially controlling the position and/or configuration of the sensor. In response to a reduction in tension in the tether, the sensor transforms from a first position to a second position. This transformation may, directly or indirectly, cause retraction of the needle. The retraction may be caused by a purely mechanical action or, alternatively, may involve an electrical signal received and/or generated by power and control system 400.

In other embodiments, the sensor may be a strain gauge, load cell, force sensor or other sensor which is configured to measure and/or monitor the strain, load, or tension present in the tether. In these embodiments, the sensor is at least partially affixed to the tether and generates an electrical signal based on the tension of the tether. The electrical signal may vary in magnitude in proportion to the magnitude of tension in the tether. Alternatively, the signal may be either interrupted or initiated when the tension in the tether falls below or exceeds a specified magnitude. The signal may be monitored by the power and control system which, based on the presence, absence, or magnitude of the signal, may cause or allow the retraction of the needle and/or cannula.

In still other embodiments, a mechanical failure of the tether may directly cause an electrical signal to be initiated or interrupted. For example, the tether may be constructed, at least partially, from a conductive material. The tether may be in electrical communication with the power and control system. The mechanical failure of the tether may interrupt a current path through the tether and cause a change in the flow of current in one or more circuits. This change may initiate or allow the retraction of the needle.

Additionally, or alternatively, the position and/or velocity of one or more features of the drive system may be monitored by a sensor such as: an optical sensor, such as an encoder; a potentiometer; or a transducer. If the position and/or velocity of the monitored feature exceeds or falls below a specified threshold, the power and control system may initiate and/or allow retraction of the needle.

A similar mechanism may be used to transform travel limiter 2229 from a configuration in which it restricts axial motion of manifold guide 2220 to a configuration in which it allows manifold guide 2220 to axially translate in the distal direction, thereby allowing for retraction of the needle from the target. For example, travel limiter 2229 may be caused to flex at living hinge feature 2229D, causing travel limiter 2229 to transform to its "open" position.

A method of operating an insertion mechanism according to the present invention includes: removing one or more lockout pins from corresponding one or more locking windows of an insertion mechanism housing, wherein removal of said lockout pins permits an insertion biasing member to expand from its initially energized state; driving, by expansion of the insertion biasing member, a clip retainer and manifold guide axially in the distal direction to force a needle at least partially out of the insertion mechanism and into a target; maintain the needle in an administration position, as it would be when inserted into the target for fluid delivery; rotating a clip retainer and a clip; permitting outwards flexion of a clip retained in a chamber of a clip retainer, wherein said clip initially retains a hub and a retraction biasing member in an energized state and wherein flexion disengages one or more release surfaces of the clip from contact with a hub thereby permitting expansion of the retraction biasing member axially in the proximal direction; and retracting the needle upon retraction of the hub through a fixed connection between the needle and the hub.

In another embodiment, a method of operating an insertion mechanism according to the present invention includes: removing one or more lockout pins from corresponding one or more locking windows of an insertion mechanism housing, wherein removal of said lockout pins permits an insertion biasing member to expand from its initially energized state; driving, by expansion of the insertion biasing member, a manifold guide axially in the distal direction to force a needle at least partially out of the insertion mechanism and into the target; maintain the needle in an administration position for fluid delivery; transforming or displacing a travel limiter, permitting additional distal displacement of the manifold guide; permitting outwards flexion of a clip retained in a chamber of the manifold guide, wherein said clip initially retains a hub and a retraction biasing member in an energized state and wherein flexion disengages one or more release surfaces of the clip from contact with a hub thereby permitting expansion of the retraction biasing member axially in the proximal direction; and retracting the needle upon retraction of the hub through a fixed connection between the needle and the hub.

Certain optional standard components or variations of the insertion mechanism or drug pump 10 are contemplated while remaining within the breadth and scope of the present invention. For example, upper or lower housings may optionally contain one or more transparent or translucent windows 18, as shown in FIGS. 1A-1C, to enable the user to view the operation of the drug pump 10 or verify that drug dose has completed. Additionally, the drug pump 10 may contain an adhesive patch 26 and a patch liner 28 on the bottom surface of the housing 12. The adhesive patch 26 may be utilized to adhere the drug pump 10 to the target for delivery of the drug dose. As would be readily understood by one having ordinary skill in the art, the adhesive patch 26 may have an adhesive surface for adhesion of the drug pump to the target. The adhesive surface of the adhesive patch 26 may initially be covered by a non-adhesive patch liner 28, which is removed from the adhesive patch 26 prior to placement of the drug pump 10 in contact with the target. Adhesive patch 26 may optionally include a protective shroud that prevents actuation of the optional sensor 24 and covers the base opening of the insertion mechanism. Removal of the patch liner 28 may remove the protective shroud or the protective shroud may be removed separately. Removal of the patch liner 28 may further remove the sealing membrane of the insertion mechanism, opening the insertion mechanism to the target for drug delivery.

Similarly, one or more of the components of the insertion mechanism and drug pump 10 may be modified while remaining functionally within the breadth and scope of the present invention. For example, as described above, while the housing of drug pump 10 is shown as two separate components upper housing 12A and lower housing 12B, these components may be a single unified component. Similarly, while guide protrusions 2204 are shown as a unified pre-formed component of insertion mechanism housing 2202, it may be a separate component fixedly attached to the interior surface of the insertion mechanism housing 202. As discussed above, a glue, adhesive, or other known materials or methods may be utilized to affix one or more components of the insertion mechanism and/or drug pump to each other. Alternatively, one or more components of the insertion mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the insertion mechanisms and drug pumps disclosed herein provide an efficient and easily-operated system for automated drug delivery from a drug container. The novel embodiments described herein provide integrated safety features; enable direct user activation of the insertion mechanism; and are configured to maintain the sterility of the fluid pathway. As described above, the integrated safety features include optional sensors, redundant lock-outs, automated needle insertion and retraction upon user activation, and numerous user feedback options, including visual and auditory feedback options. The novel insertion mechanisms of the present invention may be directly activated by the user. For example, in at least one embodiment the lockout pin(s) which maintain the insertion mechanism in its locked, energized state are directly displaced from the corresponding lockout windows of the insertion mechanism housing by user depression of the activation mechanism. Alternatively, one or more additional components may be included, such as a spring mechanism, which displaces the lockout pin(s) upon direct displacement of the activation mechanism by the user without any intervening steps.

Furthermore, the novel configurations of the insertion mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, housing and other components of the pump drug may readily be configured to accept and operate insertion mechanism 200, insertion mechanism 2000, or a number of other variations of the insertion mechanism described herein.

Assembly and/or manufacturing of the insertion mechanism, drug pump 10, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The insertion mechanism may be assembled in a number of methodologies. In one method, a hub is initially connected to a proximal end of a needle. The hub and needle are inserted into an inner chamber of a clip retainer, wherein a retraction biasing member is maintained in an energized state between the clip retainer and the hub. The hub, needle, and retraction biasing member are held in this alignment by a clip, wherein the clip is fixedly and flexibly connected to the clip retainer at a clip interface. One or more septa are inserted into the manifold to create a manifold header. The manifold and septum are inserted into a lower chamber of the manifold guide such that the needle pierces through the septum. A sterile boot is connected to the manifold, wherein the needle resides within the sterile boot when the latter is in an expanded configuration.

An insertion spring is inserted into the insertion mechanism housing between the housing and one or more guide protrusions extending into the interior of the housing from the housing cap. The manifold guide and clip retainer, having the components attached thereto as described herein, is inserted into the insertion mechanism housing such that the guide protrusions extend through corresponding passthroughs on a clip retainer flange and manifold guide ring aspect of the manifold guide. As the clip retainer and manifold guide is translated in the proximal direction, the insertion biasing member is caused to contact the manifold guide ring and become energized. As translation of the clip retainer and manifold guide and compression of the insertion biasing member reach a point above one or more lockout windows of the insertion mechanism housing, one or more corresponding lockout pin(s) may be inserted to retain the manifold guide in this position and the insertion biasing member in the compressed, energized state. A travel limiter may further be inserted into the housing such that the prongs of the travel limiter engage the aperture of the housing.

The distal end of the sterile boot may be positioned and held in fixed engagement with the distal end of the insertion mechanism housing by engagement of the housing with a base. In this position, the sterile boot is in an expanded configuration around the needle and creates an annular volume which may be sterile. A fluid conduit may be connected to the manifold at a manifold intake such that the fluid pathway, when open, travels directly from the fluid conduit, through the manifold intake, into the manifold header, and through the needle. A fluid pathway connection may be attached to the opposite end of the fluid conduit. The fluid pathway connection, and specifically a sterile sleeve of the fluid pathway connection, may be connected to a cap and pierceable seal of the drug container. The plunger seal and drive mechanism may be connected to the drug container at an end opposing the fluid pathway connection. A sealing membrane may be attached to the bottom of the base to close off the insertion mechanism from the environment. The components which constitute the pathway for fluid flow are now assembled. These components may be sterilized, by a number of known methods, and then mounted either fixedly or removably to an assembly platform or housing of the drug pump.

Manufacturing of a drug pump includes the step of attaching the base of the insertion mechanism to an assembly platform or housing of the drug pump. In at least one embodiment, the attachment is such that the base of the insertion mechanism is permitted to pass through the assembly platform and/or housing to come in direct contact with the target. The method of manufacturing further includes attachment of the fluid pathway connection, drug container, and drive mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the target during operation of the device.

A method of operating the drug pump includes the steps of: activating, by a user, the activation mechanism; displacing a control arm to actuate an insertion mechanism; and actuating a power and control system to activate a drive control mechanism to drive fluid drug flow through the drug pump. The method may further include the step of: engaging an optional sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the target. The method of operation of the insertion mechanism and the drug pump may be better appreciated with reference to FIGS. 10-12 and FIG. 17, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. An insertion mechanism for a drug pump, comprising:
an insertion mechanism housing having an internal chamber;
a manifold guide disposed within the housing;
a clip retainer disposed on or adjacent the manifold guide and movably within the internal chamber, wherein one of the manifold guide and the clip retainer includes a flange;
at least one insertion biasing member initially held in an energized state within the internal chamber between the housing and the flange;
a flexible clip disposed on or within the clip retainer;
a needle having a hollow interior, a proximal end, a distal end, and at least one side port opening into the hollow interior of the needle;
a hub connected to the proximal end of the needle, the needle and hub being configured to move between an initial position and an administration position in response to a release of energy from the at least one insertion biasing member;
a retraction biasing member held in an initial locked configuration in an energized state between the hub and the clip retainer; and
a manifold including a manifold body and at least one septum, the manifold body including a manifold intake, the at least one septum and manifold body defining a manifold header within the manifold that receives a fluid through the manifold intake, and wherein the at least one side port of the needle is disposed within the manifold header being in fluid communication with the hollow interior of the needle through the at least one side port to supply the fluid to the needle when the needle is in the administration position.

2. The insertion mechanism of claim 1, configured to move the needle from the administration position to a retracted position in response to a release of energy from the retraction biasing member, and wherein the at least one side port is not disposed within the manifold header when the needle is in the retracted position.

3. The insertion mechanism of claim 1, wherein the flexible clip includes one or more arms, each arm having a release surface and a lockout surface, wherein, in the initial locked configuration, the release surfaces engage the hub to maintain the retraction biasing member in the energized state, and wherein, in an unlocked configuration, the release surfaces disengage the hub to permit de-energizing of the retraction biasing member, thereby retracting the hub and the needle.

4. The insertion mechanism of claim 3, wherein movement of the clip retainer to produce the unlocked configuration includes an axial distal movement.

5. The insertion mechanism of claim 4, further comprising a travel limiter engaged with the housing, at least a portion of the travel limiter located within the housing internal chamber.

6. The insertion mechanism of claim 5, wherein the flexible clip transforms from the initial locked configuration to the unlocked configuration by transformation of the travel limiter from a first configuration to a second configuration, whereby in the first configuration, the travel limiter restricts distal movement of the manifold guide and prevents the release surfaces of the clip from disengaging from the hub and in the second configuration, the travel limiter allows distal movement of the manifold guide to allow the release surfaces of the clip to disengage the hub.

7. The insertion mechanism of claim 3, wherein movement of the clip retainer to produce the unlocked configuration includes a rotational movement.

8. The insertion mechanism of claim 7, wherein the clip retainer is rotated from a first rotational position to a second rotational position, wherein the rotation is transmitted to the flexible clip, whereby in the first rotational position, the release surfaces of the flexible clip are prevented from disengaging the hub and in the second rotational position, the release surfaces of the clip are permitted to disengage the hub.

9. The insertion mechanism of claim 1, further comprising a base connected to a distal end of the insertion mechanism housing and a boot fixedly connected between the manifold and the base.

10. A drug pump comprising a housing, an activation mechanism, a drive mechanism and the insertion mechanism of claim 1.

11. The drug pump of claim 10, wherein the insertion mechanism further comprises one or more retraction activation mechanisms configured to act upon the clip retainer, the one or more retraction activation mechanisms selected from the group consisting of a pivot, user action on the activation mechanism, a failure of the drive mechanism, or displacement of a control arm.

12. A method of operating a drug pump comprising the insertion mechanism of claim 1, comprising:
permitting the at least one insertion biasing member to expand in a distal direction substantially along a longitudinal axis of the insertion mechanism housing from its initial energized state, wherein such expansion drives the needle from the initial position to the administration position wherein the at least one side port is disposed within the manifold header;
connecting a fluid pathway connection to a drug container; and
activating a drive mechanism to force a fluid through the fluid pathway connection, the manifold header, the at least one side port, and the needle when the needle is disposed in the administration position.

13. The method of claim 12, further comprising:
disengaging the flexible clip from engagement with the hub; and
permitting the retraction biasing member to expand in a proximal direction substantially along the longitudinal axis of the insertion mechanism housing from its initial energized state to drive retraction of the needle.

14. The method of claim 13, further comprising:
preventing insertion of the needle or retraction of the needle when the drug pump is not in contact with a target site, the drug pump has malfunctioned, the drug pump has been prematurely activated, or any combination thereof.

15. The method of claim 12, further comprising:
preventing insertion of the needle or retraction of the needle when the drug pump is not in contact with a target site, the drug pump has malfunctioned, the drug pump has been prematurely activated, or any combination thereof.

* * * * *